US012686888B2

(12) United States Patent
Rowland et al.

(10) Patent No.: US 12,686,888 B2
(45) Date of Patent: Jul. 21, 2026

(54) METHOD FOR NON-INVASIVE PRENATAL SCREENING FOR ANEUPLOIDY

(71) Applicant: QUEST DIAGNOSTICS INVESTMENTS LLC, Secaucus, NJ (US)

(72) Inventors: Charles Rowland, San Juan Capistrano, CA (US); Renius Owen, San Juan Capistrano, CA (US); Charles Strom, San Juan Capistrano, CA (US); Ke Zhang, San Juan Capistrano, CA (US)

(73) Assignee: QUEST DIAGNOSTICS INVESTMENTS LLC, Secaucus, NJ (US)

( * ) Notice: Subject to any disclaimer, the term of this patent is extended or adjusted under 35 U.S.C. 154(b) by 1004 days.

(21) Appl. No.: 16/477,126

(22) PCT Filed: Jan. 10, 2018

(86) PCT No.: PCT/US2018/013055
§ 371 (c)(1),
(2) Date: Jul. 10, 2019

(87) PCT Pub. No.: WO2018/132400
PCT Pub. Date: Jul. 19, 2018

(65) Prior Publication Data
US 2020/0255896 A1     Aug. 13, 2020

Related U.S. Application Data

(60) Provisional application No. 62/445,196, filed on Jan. 11, 2017.

(51) Int. Cl.
*C12Q 1/6883*     (2018.01)
*G16B 20/10*     (2019.01)
*G16B 20/20*     (2019.01)
*G16B 30/10*     (2019.01)
*G16B 30/20*     (2019.01)

(52) U.S. Cl.
CPC .......... *C12Q 1/6883* (2013.01); *G16B 20/20* (2019.02); *G16B 30/10* (2019.02); *G16B 30/20* (2019.02); *C12Q 2600/156* (2013.01); *G16B 20/10* (2019.02)

(58) Field of Classification Search
None
See application file for complete search history.

(56) References Cited

U.S. PATENT DOCUMENTS

2014/0195164 A1     7/2014  Lo et al.
2016/0217251 A1     7/2016  Lo et al.

FOREIGN PATENT DOCUMENTS

WO     WO-2009/013496 A1     1/2009
WO     WO-2014/043763         3/2014

OTHER PUBLICATIONS

Gil et al. Analysis of cell-free DNA in maternal blood in screening for fetal aneuploidies: updated meta-analysis Untrasound Obstetrics and Gynecology vol. 45, pp. 249-266 (Year: 2015).*
Neufeld-Kaiser et al. Positive predictive value of non-invasive prenatal screening for fetal chromosome disorders using cell-free NDA in maternal serum: independent clinical experience of a tertiary referral center BMC Medicine vol. 13, article 129 (Year: 2015).*
Zhao C, Tynan J, Ehrich M, Hannum G, McCullough R, Saldivar JS, Oeth P, van den Boom D, Deciu C. Detection of fetal subchromosomal abnormalities by sequencing circulating cell-free DNA from maternal plasma. Clin Chem. Apr. 2015;61(4):608—(Year: 2015).*
Lefkowitz RB, Tynan JA, Liu T, Wu Y, Mazloom AR, Almasri E, Hogg G, Angkachatchai V, Zhao C, Grosu DS, McLennan G, Ehrich M. Clinical validation of a noninvasive prenatal test for genomewide detection of fetal copy number variants. Am J Obstet Gynecol. Aug. 2016;215(2):227.e1-227.e16. (Year: 2016).*
Chen EZ, et al., Noninvasive prenatal diagnosis of fetal trisomy 18 and trisomy 13 by maternal plasma DNA sequencing. PLoS One. 2011;6(7):e21791 (Year: 2011).*
Liang D, Lv W, Wang H, Xu L, Liu J, Li H, Hu L, Peng Y, Wu L. Non-invasive prenatal testing of fetal whole chromosome aneuploidy by massively parallel sequencing. Prenat Diagn. May 2013;33(5):409-15. doi: 10.1002/pd.4033. Epub Jan. 9, 2013 (Year: 2013).*
Chan, K. C. Allen et al. "Second Generation Noninvasive Fetal Genome Analysis Reveals de Novo Mutations, Single-Base Parental Inheritance, and Preferred DNA Ends." Proceedings of the National Academy of Sciences—PNAS 113.50 (2016): E8159-E8168. Web. (Year: 2016).*
Stumm, Markus et al. "Noninvasive Prenatal Detection of Chromosomal Aneuploidies Using Different next Generation Sequencing Strategies and Algorithms." Prenatal diagnosis 32.6 (2012): 569-577. Web. (Year: 2012).*

(Continued)

*Primary Examiner* — Karlheinz R. Skowronek
*Assistant Examiner* — Joseph Pulliam
(74) *Attorney, Agent, or Firm* — DUANE MORRIS LLP

(57) ABSTRACT

The present disclosure provides methods for non-invasive prenatal screening (NIPS) of fetal aneuploidies. The present methods are based on analyzing cell-free fetal DNA (cff DNA) found in a pregnant woman's circulation through the next generation sequencing (NGS) technology. Particularly, the present methods analyze the relative abundance of different fetal genomic fragments present in the maternal sample, where the fragments can be aligned to particular chromosomal locations of the fetal genome. The relative abundance information is indicative as to whether a particular chromosome is overrepresented or underrepresented in a fetal genome as compared to normal individuals, and thus can be used to detect fetal aneuploidy. Additionally, methods for increasing the positive predictive values (PPV) of NIPS by excluding false-positive detections are also provided.

31 Claims, 7 Drawing Sheets

Specification includes a Sequence Listing.

(56)            References Cited

OTHER PUBLICATIONS

Bayindir, Baran et al. "Noninvasive Prenatal Testing Using a Novel Analysis Pipeline to Screen for All Autosomal Fetal Aneuploidies Improves Pregnancy Management." European journal of human genetics: EJHG 23.10 (2015): 1286-1293. Web. (Year: 2015).*

Office Action and Search Report dated Feb. 18, 2023 in CN 201880015541.8, with English translations.

Supplementary European Search Report dated Jul. 9, 2020 in EP 18738729.5.

Cirigliano, V. et al., "Performance of the neobona test: a new paired-end massively parallel shotgun sequencing approach for cell-free DNA-based aneuploidy screening," Ultrasound in Obstetrics and Gynecology, Dec. 15, 2016, vol. 49, No. 4, pp. 460-464.

International Search Report and Written Opinion Received in International Application No. PCT/US2018/013055 mailed Apr. 26, 2018.

Snyder, Matthew W. et al., "Copy-number variation and false positive prenatal Aneuploidy Screening Results," Apr. 1, 2015, The New England Journal of Medicine, vol. 372, No. 17, pp. 1639-1645.

Strom, Charles M. et al., "Improving the positive predictive value of non-invasive prenatal screening (NIPS)," PLoS One, Mar. 1, 2017, vol. 12, No. 4, pp. 1-18.

Yin, Ai-Hua et al., "Noninvasive detection of fetal subchromosomal abnormalities by semiconductor sequencing of maternal plasma DNA," Proceedings of the National Academy of Sciences of the USA, Nov. 9, 2015, vol. 112, No. 47, pp. 14670-14675.

Zhang, Han et al., "Statistical approach to decreasing the error rate of noninvasive prenatal aneuploid detection caused by maternal copy number variation," Scientific Reports, Nov. 4, 2015, vol. 5, Article 16106, pp. 1-9.

Office Action and Search Report dated Nov. 1, 2023 in CN 201880015541.8, with English translation.

Zhang et al., "Non-invasive prenatal testing for trisomies 21, 18 and 13: clinical experience from 146 958 pregnancies," Ultrasound Obstet. Gynecol., Apr. 8, 2015, 45:530-538.

Partial European Search Report in EP Application No. 25199402.6, dated Feb. 12, 2026, in 18 pages.

Snyder, Matthew W., et al. "Copy-number variation and false positive prenatal aneuploidy screening results." New England Journal of Medicine 372.17 (2015): 1639-1645, Supplementary Appendix, 15 pages.

* cited by examiner

METHOD FOR NON-INVASIVE PRENATAL SCREENING FOR ANEUPLOIDY

CROSS-REFERENCE TO RELATED APPLICATIONS

This application is the U.S. National Stage of PCT/US2018/013055, filed Jan. 10, 2018, which claims the benefit of and priority to U.S. Provisional Appl. No. 62/445,196, filed Jan. 11, 2017, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 30, 2019, is named 034827-1600_SL.txt and is 876 bytes in size.

TECHNICAL FIELD

The present disclosure provides methods for non-invasive prenatal screening (NIPS) of fetal aneuploidies. The present methods are based on analyzing cell-free fetal DNA (cff DNA) found in a pregnant woman's circulation through the next generation sequencing (NGS) technology. Particularly, the present methods analyze the relative abundance of different fetal genomic fragments present in the maternal sample, which fragments can be aligned to particular chromosomal locations of the fetal genome. The relative abundance information is indicative as to whether a particular chromosome is overrepresented or underrepresented in a fetal genome as compared to normal individuals, and thus can be used to detect fetal aneuploidy. Additionally, methods for increasing the positive predictive values (PPV) of NIPS by excluding false-positive detections are also provided.

BACKGROUND

The present invention generally relates to the field of non-invasive prenatal screening (NIPS), particularly NIPS using cell-free fetal DNA (cff DNA) found in maternal plasma. Due to biological and technical issues, current NIPS methods can produce false-positive results, prompting a medical practitioner to prescribe further diagnostic testing through invasive procedures, such as amniocentesis or a chorionic villus sampling (CVS), which carry a risk of procedure-related miscarriage and other complications. Rather than undergo such procedures, a significant number of women have terminated their pregnancies based on a NIPS report of high risk of fetal aneuploidy without additional testing. Thus, there exists a need in the field for the development of new NIPS methods, particularly those with improved positive predictive values.

SUMMARY OF THE INVENTION

In one aspect, provided herein are methods for detecting false-positive diagnosis of chromosomal aneuploidy in a fetus by a non-invasive prenatal screening (NIPS). The methods comprise (a) dividing a chromosome of interest diagnosed to be aneuploid into a plurality of bins, each bin having a chromosomal location; (b) obtaining a bin-specific test parameter for each bin; (c) plotting the bin-specific test parameters versus the chromosomal locations of corresponding bins to produce an ideogram of the chromosome of interest; and (d) detecting false-positive diagnosis when the ideogram exhibits consistent bin-specific test parameters across less than a substantial portion of the chromosome of interest. In some embodiments, the chromosome of interest is one or more chromosomes of the species under examination.

In some embodiments, the detecting step (d) is performed by detecting false-positive diagnosis when the ideogram exhibits a large-scale increase of bin-specific test parameter in at least one bin compared to remaining bins. Particularly, in some embodiments, the large-scale increase is at least 1.2 folds, at least 1.5 folds, at least 2 folds, at least 2.5 folds, at least 3 folds, at least 3.5 folds, at least 4 folds, at least 4.5 folds, at least 5 folds, at least 5.5 folds, at least 6 folds, at least 6.5 folds or at least 7 folds.

In some embodiments, the methods further comprise repeating steps (a) to (d) for a confirming chromosome other than the chromosome of interest. Particularly, in some embodiments, the confirming chromosome is one or more chromosomes of the species under examination.

In some embodiments, the substantial portion of the chromosome of interest represents more than about 2%, 5%, 10%, 20%, 30%, 40%, 50%, 60%, 70%, 80%, or 90% of the chromosome of interest.

In some embodiments, the bin-specific parameter is reflective of relative abundance of genetic material corresponding to the bin in a maternal test sample. Particularly, in some embodiments, obtaining the bin-specific test parameter comprises sequencing cell-free DNA from a maternal test sample of a pregnant woman carrying the fetus to provide sequence reads. In some embodiments, obtaining the bin-specific test parameter comprises aligning the sequence reads to one or more bins of a reference genome comprising the chromosome of interest. In some embodiments, obtaining the bin-specific test parameter comprises calculating the bin-specific test parameter based on a total number of sequence reads aligned to each bin. In some embodiments, the bin-specific test parameter is a normalized bin read count. In some embodiments, the bin-specific test parameter is produced by the NIPS.

In some embodiments, the present methods improves a positive predictive value (PPV) of the NIPS to at least 30%, 35%, 40%, 45%, 50%, 55%, 60%, 65%, 70%, 75%, 80%, 85%, 90%, or 95% for human trisomy 21, human trisomy 18 and/or human trisomy 13. Particularly, in some embodiments, the PPV is improved to at least 93% for human trisomy 21, at least 72% for human trisomy 18, and/or at least 39% for human trisomy 13. In some embodiments, the PPV for trisomy 21 is improved to 98% for human trisomy 21, 92% for human trisomy 18, and/or 69% for human trisomy 13.

In some embodiments, the present methods improve a positive predictive value (PPV) of the NIPS by at least 4%, 10%, 20%, 30%, 40% and 50% for human trisomy 21, human trisomy 18 and/or human trisomy 13. Particularly, in some embodiments, the PPV is improved by at least 4% for human trisomy 21, at least 20% for human trisomy 18, and/or at least 30% for human trisomy 13.

In another aspect, provided herein are methods for detecting false-positive diagnosis of chromosomal aneuploidy in a fetus by a non-invasive prenatal screening (NIPS) are provided. Particularly, the methods comprise (a) dividing a reference chromosome into a plurality of bins, each bin having a chromosomal location; (b) obtaining a bin-specific parameter for each bin; (c) calculating a first sum of bin-specific test parameters for corresponding bins residing on a confirming chromosome; wherein the confirming chromosome is different from a chromosome of interest diagnosed to be aneuploid; (d) calculating a second sum of bin-specific test parameters for corresponding bins residing on one or more autosomes; (e) calculating a chromosome representation value for the confirming chromosome by dividing the first sum by the second sum; (f) comparing the chromosome representation value to a set of references to generate a chromosome-specific comparison result; (g) detecting false-positive diagnosis when the chromosome-specific comparison result achieves a pre-determined threshold. In some embodiments, the confirming chromosome is one or more chromosomes in the reference genome.

In some embodiments, obtaining a bin-specific parameter for each bin is performed by sequencing cell-free DNA from a maternal test sample of a pregnant woman carrying the fetus to provide sequence reads; wherein the fetus has been diagnosed to be aneuploid of a chromosome of interest; aligning the sequence reads to one or more bins of the reference genome; and calculating the bin-specific test parameter based on a total number of sequence reads aligned to each bin. In some embodiments, the bin-specific test parameter is a normalized bin read count.

In some embodiments, the set of references comprises a plurality of chromosome representation values for the confirming chromosome obtained from a random sample of unaffected pregnancies.

In some embodiments, step (f) is performed by calculating a Z-score of said test chromosome representation value with respect to the set of references. In some embodiments, the threshold is achieved when the Z-score is greater than 4 or greater than 8.

Further, in any of the embodiments above, the fetal aneuploidy can be a complete or partial chromosomal duplication or a chromosomal trisomy, such as trisomy 13, trisomy 18 or trisomy 21 of the human genome. The reference genome can be a human reference genome and the fetus can be an aneuploid mosaic individual. Additionally, in any of the embodiments above, the method can further comprise first assessing a fetal fraction of the cell-free DNA in the maternal test sample before performing step (a). In some embodiments, the maternal test sample is excluded when the fetal fraction is less than 4%.

DETAILED DESCRIPTION

Figure 1:
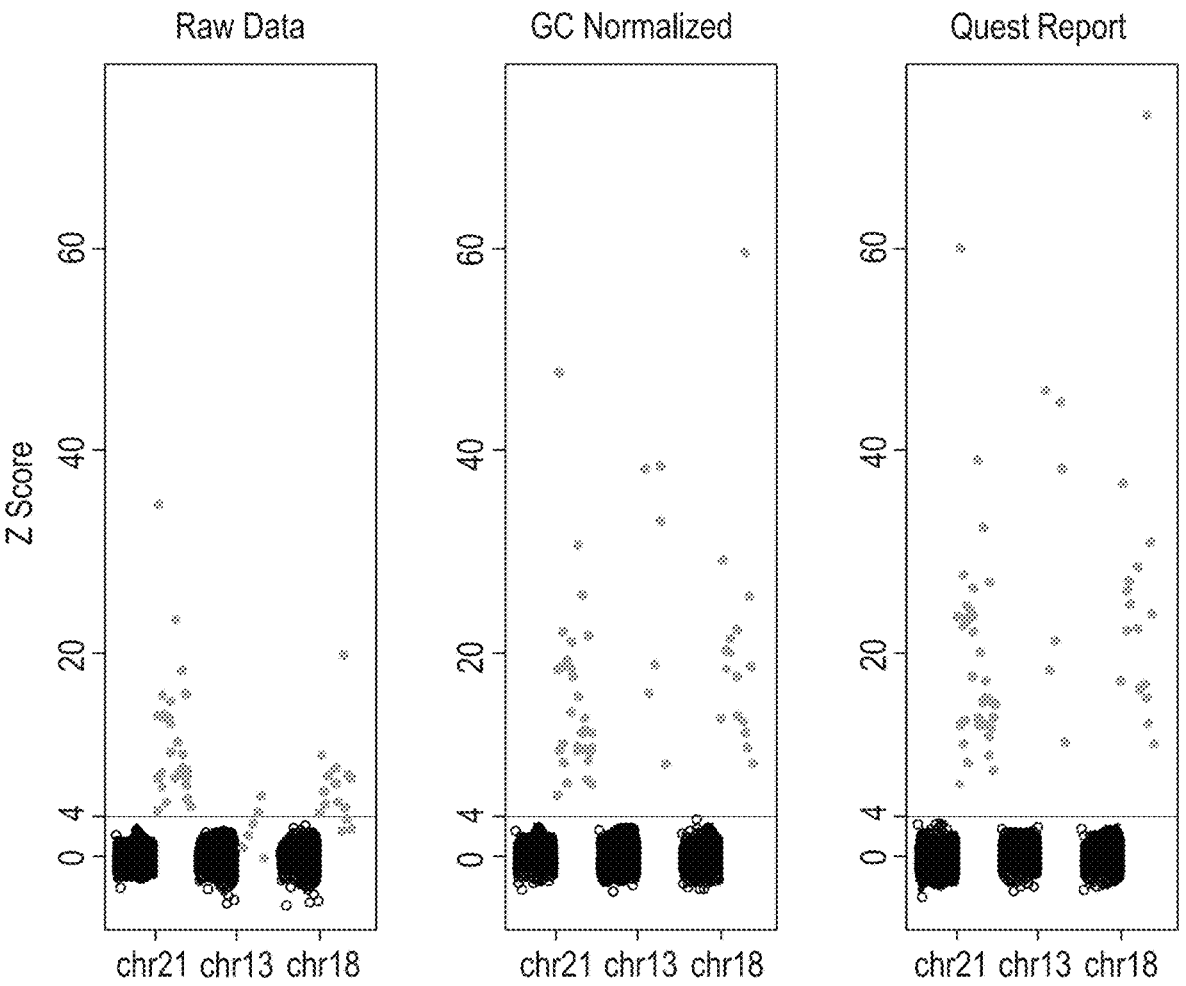
FIG. 1 shows Z-scores of the present NIPS assay for trisomies 21, 18, and 13 before (Raw Data) and after correction for GC content (GC Normalized) and statistical smoothing using a proprietary software algorithm (Quest Report). As shown in the figure, the assay provided complete discrimination between affected and unaffected pregnancies for trisomy 21, even without adjustments. GC correction and statistical smoothing eliminated the substantial overlap between affected and unaffected pregnancies for trisomies 18 and 13, and enhanced separation for trisomy 21.

The present disclosure provides methods for non-invasive prenatal screening (NIPS) of fetal aneuploidies. The present methods are based on analyzing cell-free fetal DNA (cff DNA) found in a pregnant woman's circulation through the next generation sequencing (NGS) technology. Particularly, the present methods analyze the relative abundance of different fetal genomic fragments present in the maternal sample, where the fragments can be aligned to particular chromosomal locations of the fetal genome. The relative abundance information is indicative as to whether a particular chromosome is overrepresented or underrepresented in a fetal genome as compared to normal individuals, and thus can be used to detect fetal aneuploidy. Additionally, methods for increasing the positive predictive values (PPV) of NIPS by excluding false-positive detections are also provided.

The term "karyotype" is well-recognized in the field and refers to an organized profile of an organism's chromosomes, indicating the copy numbers of each chromosome in the genome. Different species of organisms may have different numbers of chromosomes in their genome, and thus different karyotypes. For example, the normal human karyotypes contain 22 pairs of autosomal chromosomes (autosome) and one pair of sex chromosomes (allosomes). Normal karyotypes for female humans contain two X allosomes; and normal male humans have both an X and a Y allosomes.

The term "ploidy" refers to the number of sets of chromosomes contained in the species' genome. Particularly, a haploid species has a single set of chromosomes, each chromosome not being part of a pair. A diploid species has two homologous copies of each chromosome. By extension, a cell may be called haploid or diploid if its nucleus is haploid or diploid, and an organism may be called haploid or diploid if its somatic cells are haploid or diploid. Nearly all mammals, including human, are diploid organisms.

The terms "aneuploidy" and "aneuploid" are terms well recognized in the art and refer to the presence of an abnormal number of chromosomes in a cell of an organism, which differs from the usual karyotype for that species. For example, because a normal human cell has 46 chromosomes, including 22 pairs of autosomes and 1 pair of sex chromosomes, a human cell having 45 or 47 chromosomes instead of the usual 46 is aneuploid. Aneuploidy may result from an error in the cell division process, where the "daughter" cells formed have the wrong number of chromosomes. In some cases there is a missing chromosome (monosomy), while in others an extra (trisomy). Both monosomy and trisomy are common causes of genetic disorders in human, including certain birth defects and cancers. In human, apart from sex chromosome disorders, most cases of aneuploidy result in miscarriage. The most common autosomal trisomy among live birth is trisomy of chromosomes 21, 18, or 13. For example, the Down Syndrome is a genetic disorder caused by the presence of all or part of a $3^{rd}$ copy of chromosome 21.

The term "trisomy" refers to a type of aneuploidy in a diploid organism, where there is an extra copy (three copies) of a particular chromosome, instead of the normal two copies of a pair. The term "monosomy" also refers to a form of aneuploidy in a diploid organism, where there is one missing copy (only one copy) of a particular chromosome, rather than the normal two copies in a pair.

The term "mosaicism" or "mosaic" as used herein refers to the presence of two or more cell lines with different karyotypes in the same individual. For example, in some embodiments, a mosaic individual may have certain populations of aneuploid somatic cells, while the other cells have the normal karyotype.

The term "fetal aneuploidy" as used herein refers to aneuploidy in a fetus in gestation. Diagnosis of such disorder may be through invasive or non-invasive methods.

The terms "non-invasive prenatal testing (NIPT)" and "non-invasive prenatal screening (NIPS)" are used interchangeably herein and refer to maternal sample tests for fetal aneuploidy, such as selected chromosome trisomies, based on detecting cell-free fetal DNA presented in a maternal sample, such as a maternal blood sample.

The term "invasive prenatal examination" as used herein refers to methods for pre-natal examination on a fetus via a probe or probes placed inside the fetus-containing space of a pregnant women's body or a maternal tissue directly connecting to the fetus, such as the uterus, placenta, or umbilical cord. Invasive prenatal examinations that have been contemplated to be used in connection with the present disclosure include but are not limited to amniocentesis and chorionic villus sampling.

The term "chromosomal duplication" as used herein refers to duplication of an entire chromosome or a portion of a chromosome. Depending on the contexts, the term "complete chromosomal duplication" may refer to the duplication of a whole chromosome, and the term "partial chromosomal duplication" may refer to duplication of a portion of a chromosome. For example, in some embodiments, a partial chromosomal duplication refers to the existence of duplicated genetic material corresponding to more than 2%, 5% 10%, 20%, 30%, 40%, 50%, 60%, 70%, 80%, or 90% of a particular chromosome in a genome. In other embodiments, a partial chromosomal duplication refers to the duplication of hundreds of kilo base pairs to tens of mega base pairs of genetic materials of a particular chromosome in a genome.

The term "chromosomal deletion" as used herein refers to the loss of an entire chromosome or a portion of a chromosome. In some embodiments, in a case of partial chromosomal deletion, the genome may lose more than 2%, 5% 10%, 20%, 30%, 40%, 50%, 60%, 70%, 80%, or 90% of a particular chromosome. In some embodiments, partial chromosomal deletion refers to the loss of hundreds of kilo base pairs to tens of mega base pairs of genetic materials of a particular chromosome in a genome.

Chromosomal duplication or deletion may arise as the product of various types of errors in DNA replication or repair machinery, as well as through fortuitous capture of genetic elements by the chromosome. As used herein, duplicated or deleted regions of a chromosome may or may not contain any gene.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "chromosome variation" as used herein refers to the phenomenon that chromosomes vary slightly in composition and size among individuals of a species. For example, copy number variation refers to the observed phenomenon that sections of a species' genome are repeated and the number of repeats in the genome varies among individuals in the population. Additionally, microduplication and microdeletion refer to chromosome variations in which a small amount of genetic material on a chromosome is abnormally copied or deleted in an individual's genome. Further, chromosomal duplication or deletion may occur over an extended span of genomic region. Depending on the context, chromosome variations may or may not produce observable phenotypic abnormality in the individuals. Thus, chromosomes may vary in composition and size among different individuals of a species due to inherited or de novo chromosome variations.

The terms "cell-free DNA (cfDNA)" as used herein refers to any free-floating DNA existing in a sample, such as the blood plasma of a pregnant patient. Cell-free DNA found in a pregnant woman's blood may contain DNA both originated from the mother and the fetus. The term "cell-free fetal DNA (cffDNA)" as used herein refers to fetal DNA circulating freely in the maternal system, such as in the mother's bloodstream. Through various mechanisms, cffDNA may, for example, originate from the trophoblasts making up the placenta. In some cases, the fetal DNA may be fragmented and make its way into the maternal bloodstream via shedding of the placental micro-particles into the maternal bloodstream. In some cases, cffDNA can first be observed in maternal blood as early as 7 weeks gestation, and increases in the amount as the pregnancy progresses. The cffDNA may be sampled by venipuncture on the mother and provides the basis for non-invasive prenatal diagnosis and testing.

The term "fetal fraction (ff)" as used herein refers to the percentage of cell-free DNA found in a pregnant mother's test sample that originates from the fetus. For example, if 10% of cell-free DNA found in a mother's blood sample is of a fetal origin, the fetal fraction (ff) is determined to be 10%. In some embodiments, fetal fraction is used as a parameter for sample quality and for determining whether a maternal sample should be included in the analysis. Particularly, in some embodiments, when the fetal fraction of a sample is below a pre-determined threshold, the maternal sample is excluded. In some embodiments, the threshold ranges between about 1% to about 5%. In some embodiments, the threshold is about 4%.

"Next generation sequencing (NGS)" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, the term "library" refers to a collection of nucleic acid sequences, e.g., a collection of nucleic acids derived from whole genomic, sub-genomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The term "sequencing bin" or simply "bin" is well-recognized in the field and refers to a chromosomal region which has a characteristic DNA sequence known to be unique to that chromosomal region. A bin thus has a chromosomal location corresponding to the particular region on a chromosome. In various embodiments, a bin may be 5 kilo base pairs (kbp), 10 kbp, 20 kbp, 30 kbp, 40 kbp, 50 kbp, 70 kbp, 80 kbp, 90 kbp, 100 kbp, 150 kbp, 200 kbp, 300 kbp, 400 kbp or 500 kbp long.

A "sequence read" or simply "read" as used herein refers to sequence information of a nucleic acid fragment obtained through a sequencing assay, such as a next generation sequencing (NGS) assay. Thus, if a sequence read aligns with the characteristic sequence of a bin, the sequence read can be unambiguously mapped to the bin and its specific chromosomal location. The term "bin read count" or simply "bin count" refers to the total number of reads mapped to a bin. In some embodiments, a bin read count can be a raw bin read count or a normalized bin read count.

The term "reference genome" refers to a nucleic acid sequence database, assembled as a representative example of a species' partial or complete set of genetic constitution, such as DNA sequences of particular chromosomes contained in the species' genome. For example, in one embodiment, human reference genome is maintained and improved by the Genome Reference Consortium (GRC). The GRC continues to improve reference genomes by building new sequence alignments that contain fewer gaps in the genome. For example, the human reference genome GRCh38 is the twentieth version of human reference genome released by the GRC.

The term "Z-score" refers to a numerical measurement of a relationship between the value in question (the sample value) and the data set to which the data point belongs. Particularly, the Z-score measures the difference between the sample value and the centrality of distribution in terms of the spread of the distribution of the set of data points. In some embodiments, the centrality of distribution can be measured as the median or mean value of the data set. In some embodiments, the spread of the distribution may be measured as the standard deviation or median absolute deviation of the data set. More particularly, in some embodiment, a Z-score indicates how many median absolute deviations above or below the median the sample value is. Particularly, Z-score can be calculated by $z=(X-\mu)/\sigma$, where X represents the sample value; $\mu$ represents the median; and a represents the median absolute deviation of the data set. Thus, a z-value equals to zero indicates that the sample value is identical to the median. A positive z-value indicates that the sample value is greater than the median, and a negative Z-score indicates that the sample value is less than the median.

The term "ideogram" as used herein refers to a schematic representation of one or more chromosomes. An ideogram can show, among others, the relative sizes of the chromosomes and their banding patterns, which may appear when a tightly coiled chromosomal region is stained and viewed under a microscope. As used herein, an ideogram can also show mapping of characteristic DNA sequences, including but not limited to, known gene sequences, marker sequences, bin sequences, to a particular chromosomal location. In some embodiments, mapping of a characteristic DNA sequence to a chromosomal location is associated with a value assigned to that chromosomal location. In some embodiments, such value can be a bin read count or a Z-score.

"Positive predictive value (PPV)" of a test for a disorder is proportional to the test's specificity and the prevalence of the disorder in the population. For example, a test with 100% sensitivity and 99% specificity (false-positive rate of 1%) for a disorder with a prevalence of 1:100 (1%) will have a PPV of only 50%, since for every 100 tests there will be approximately 1 true-positive and 1 false-positive result. In some embodiments, the prevalence of trisomies 21 is set to be 1:185, trisomy 18 is 1:470, and trisomy 13 is 1:1500.

Certain invasive procedures for detecting fetal aneuploidies carry a risk of procedure-related miscarriage and other complications. See for example Tabor et al. "Update on procedure-related risks for prenatal diagnosis techniques." *Fetal Diagn Ther.* 2010; 27: 1-7 and Benn et al. "Position statement from the Aneuploidy Screening Committee on behalf of the Board of the International Society for Prenatal Diagnosis." *Prenat Diagn.* 2013; 33: 622-629.

Accordingly, in one aspect of the present disclosure, provided are methods for noninvasive prenatal screening using cell-free fetal DNA contained in a maternal test sample. For non-invasive prenatal testing, the maternal test sample can be obtained from a pregnant woman without physically invading the fetus-containing space of the body or any maternal tissue directly connecting to the fetus. Exemplary embodiments of a maternal test sample include whole blood samples, plasma samples, tissue samples, urine samples, saliva samples, hair samples, feces and other types of biological specimens that can be non-invasively collected from the pregnant woman.

Particularly, the maternal test sample also contains a sufficient amount of cell-free fetal DNA, such that information of the fetal genome can be analyzed according to the methods provided herein. In certain embodiments, the maternal test sample can also contain cell-free DNA that originates from the maternal genome. For example, circulating cell-free DNA in the plasma of pregnant woman may be a mixture of placental fetal DNA and maternal DNA. In some embodiments, the cell-free fetal DNA is present in a wide background of maternally-originated DNAs. Thus, alternations in the amount of genetic material attributable to the fetal genome may be diluted by maternal contributions. Accordingly, in some embodiments, the maternal test sample is evaluated for the fetal fraction of cell-free DNA. Preferably, the fetal fraction is sufficient such that genetic composition of the fetal genome can be analyzed according to the methods provided herein.

In some embodiments, the fetal fraction of cell-free DNA contained in a maternal sample is measured. Samples having a fetal fraction below a certain threshold can be excluded from analysis. In some embodiments, maternal test samples of less than about 1% fetal fraction are excluded. In some embodiments, maternal test samples of less than about 2% fetal fraction are excluded. In some embodiments, maternal test samples of less than about 3% fetal fraction are excluded. In some embodiments, maternal test samples of less than about 4% fetal fraction are excluded. In some embodiments, maternal test samples of less than about 5% fetal fraction are excluded.

Various methods can be used to quantify cell-free fetal DNA and to establish the fetal fraction of a sample. For example, in some embodiments, for male-bearing pregnancies, the presence of Y chromosome-specific sequences, such as SRY, can be quantified to establish the fetal fraction of cell-free DNA in a maternal sample. In other embodiments, for male or female-bearing pregnancies, paternally-inherited fetal single nucleotide polymorphism (SNP) alleles can be quantitated to establish the fetal fraction. In other embodiments, for male or female-bearing pregnancies, different methylation characteristics of fetal DNA and maternal DNA can be distinguished and respectively quantitated to establish the fetal fraction. In various embodiments, DNA quantitation techniques such as real-time polymerase chain reaction (RT-PCR) can be used.

In some embodiments, establishing the fetal fraction can be based on next-generation sequencing (NGS) data. Particularly, in some embodiments, total cell-free DNA in a maternal test sample is sequenced via next-generation sequencing technology to generate a plurality of DNA sequence reads. Then, the sequence reads are aligned to various bins residing on one or more chromosomes of a reference genome.

In some embodiments, for male-bearing pregnancies, fetal fraction can be calculated as:

$$2 \times \left(1 - \overline{N}_{23} / \overline{N}\right)$$

where $\overline{N}_{23}/\overline{N}$ is average bin read count for chromosome X normalized to the average bin read count for all autosomes.

In some embodiments, male fetal fraction is estimated based on X chromosome underrepresentation in the test sample. Particularly, in some embodiments, NGS data are processed by the published Reliable Accurate Prenatal non-Invasive Diagnosis R package (RAPIDR). In other embodiments, X chromosome underrepresentation is estimated using a non-pregnant female as the two X chromosome copy reference, a male as the single X chromosome copy reference or pregnant samples of known fetal fractions as standard controls.

In some embodiments, male fetal fraction is estimated based on Y chromosome overrepresentation in a sample. Particularly, in some embodiments, Y chromosome overrepresentation is estimated using a non-pregnant female as the Y chromosome absence (0% Y) reference, a male as the Y chromosome presence (100% Y) reference and known pregnant samples of known fetal fractions as standard controls.

In some embodiments, for female-bearing pregnancies, fetal fraction is estimated using a regularized regression model. For example, in some embodiments, male fetal fractions are estimated for a training set of multiple male-bearing pregnancies. The estimated male fetal fractions are used to model fetal fraction as a function of a sample's bin counts normalized by the sample's total read count before GC-bias correction The model is then used to estimate fetal fraction for female-bearing pregnancies. In some embodiments, bins residing on chromosomes 13, 18, 21, X or Y chromosomes are excluded from the modeling process. In some embodiments, the model is a regularized linear regression model. Particularly, in some embodiments, the model is a Lasso and Elastic-Net Regularized Generalized Linear Model (GLMNET). In some embodiments, ten-fold cross-validation using an alpha parameter of 1 is used to select the lambda parameter having the minimum cross-validated error for use in building the final model.

Further in some embodiments, estimation of fetal fraction is based on more than one of the methods as described above. For example, in some embodiments, fetal fraction estimates given by two or more different methods are averaged to produce the final estimate of fetal fraction in a sample.

In some embodiments, cell-free DNA contained in a maternal sample is analyzed for the detection of fetal aneuploidy. Particularly, in some embodiments, the maternal test sample is non-invasively collected from a pregnant woman. In some embodiments, the pregnant woman has been previously determined to be at high risk of producing an aneuploid progeny. In some embodiments, the pregnancy has been previously determined to be at high risk of being aneuploid. In some embodiments, individuals or pregnancies deemed to be at high risk include women aged 35 or above, with ultrasonographic findings suggesting an increased risk of fetal aneuploidy, having previous pregnancy affected by aneuploidy or parental balanced Robertsonian translocation associated with trisomy 21, 13, and those screened positive for high risk aneuploidy by conventional first or second trimester screening tests. In some embodiments, the present methods are used to detect fetal aneuploidy for singlet or twin pregnancies.

Particularly, in some embodiments, cell-free DNA from a maternal test sample obtained from a pregnant woman is sequenced with next generation sequencing technique. Particularly, in some embodiments, shotgun (genome wide) massively parallel sequencing (s-MPS) is used. In some embodiments, s-MPS relies on identification and counting of large numbers of DNA fragments in maternal specimens. MPS is used to simultaneously sequence millions of genome-wide fetal and maternal fragments and informative sequences are mapped to discrete locations on all chromosomes. Thus, for example, if fetal trisomy is present, there will be a relative excess of counts for a given chromosome and with a monosomy deficit.

In some embodiments, nucleic acid fragments contained in the maternal test sample are sequenced to produce a plurality of sequence reads. In some embodiments, the plurality of sequence reads are aligned to one or more bins of a reference genome, each bin is residing on a chromosome of the reference genome and having a chromosomal location. A raw bin read count is calculated for each bin by counting the total number of sequence reads mapped to the bin.

In some embodiments, the raw bin read count is normalized to remove artifacts such as individual sample variations, GC-sequencing biases, and other artifacts due to chromosome's high-order structures, etc. In various embodiments, a normalized bin read count can be obtained by processing a corresponding raw bin read count via one or more normalization steps as described below.

Particularly, in some embodiments, a raw bin read count can be scaled by dividing the raw bin read count by the sum of autosomal bin read counts of the sample. In some embodiments, the scaled bin read count is further corrected by subtracting sequencing bias caused by varying GC-content across the genome, and the result is centered at the median of the scaled autosomal bin read counts. In some embodiments, the corrected bin read counts is further scaled by multiplying the total number of bins in the assay.

In some embodiments, samples from a reference population of presumably unaffected pregnancies are also obtained and analyzed. Particularly, for each reference sample, raw bin counts are obtained and processed as described above. Thus, the reference population provides a set of reference bin read counts for each bin that is analyzed for the sample in question. In some embodiments, a median value is calculated based on the set of reference bin read counts for each bin.

In some embodiments, bin read counts of the sample in question is also scaled (divided) by the median reference bin read count of the corresponding bin. The result is centered around 1 and further corrected by subtracting the median of the sample's autosomal bin read counts.

In some embodiments, high order artifacts are corrected as defined by a regression of normalized bin read counts of the sample versus the first ten principal components among the normalized bin read counts determined from a reference population of presumably unaffected samples.

In some embodiments, a bin-specific test parameter is calculated for each bin based on the total number of sequence reads aligned to the bin. In some embodiments, the bin-specific test parameter is the raw bin read count. In other embodiments, the bin-specific test parameter is a normalized bin read count that is generated by processing the raw bin read count by one or more normalization steps described above.

In some embodiments, the relative abundance of genetic materials originating from individual fetal chromosomes in the sample are determined for the detection of fetal aneuploidy. Particularly, in some embodiments, representation of one or more chromosome of interest in a sample is calculated. The level of representation of individual chromosomes is reflective of the relative abundance of the individual chromosomes present in the sample fetal genome. Particularly, in some embodiments, chromosomal representation of a particular chromosome of interest $chrRep_i$ can be calculated as $$chrRep_i = \frac{chrTotalRC_i}{\sum_{j=1\ldots22} chrTotalRC_j}$$

where $chrTotalRC_i$ denotes the sum of bin-specific parameters of bins residing on a chromosome of interest, and $\sum_{j=1\ldots22} chrTotalRC_j$ denotes the sum of bin-specific parameters of bins residing on all autosomes of the reference genome.

In some embodiments, to determine whether a particular chromosome of interest is overrepresented or underrepresented in a sample, the chromosomal representation value of the sample is compared to a reference indicative of the normal representation. Particularly, in some embodiments, representation of the chromosome of interest is determined for samples collected from a reference population of presumably unaffected pregnancies. The chromosomal representation value of the sample in question is then compared to the set of chromosomal representation values determined from the reference population. Particularly, in some embodiments, a chromosome-specific Z-score indicative of the relationship between the sample chromosomal representation and the set of reference chromosomal representation values is calculated as:

$$Z = (x - \mu)/\sigma$$

where X is the sample chromosomal representation; $\mu$ is the median value of the set of reference chromosomal representations; and $\sigma$ is the median absolute deviation (MAD) of the set of reference chromosomal representations.

The Z-score indicates how many standard deviations above or below the mean the sample value is. Accordingly, in some embodiments, a Z-score equals or close to zero indicates that the sample chromosomal presentation of the chromosomal of interest is identical or very similar to the mean chromosomal representation in unaffected pregnancies; a Z-score significantly greater than zero indicates that the chromosome of interest is overrepresented in the sample as compared to unaffected pregnancies; and a Z-score significantly lower than zero indicates that the chromosome of interest is underrepresented in the sample as compared to unaffected pregnancies. Particularly, in some embodiments, a Z-score>4 indicates chromosome overrepresentation. In some embodiments, a Z-score>4 indicates a high risk of fetal chromosomal trisomy. In some embodiments, a Z-score>3 but <8 suggests that further diagnostic tests for fetal aneuploidy are advisable for the pregnant patient, such as invasive prenatal diagnostic tests. In some embodiments, a Z-score≥8 indicates chromosome overrepresentation. In some embodiments, a Z-score≥8 indicates a high risk of fetal chromosomal trisomy. In some embodiments, a Z-score≥8 suggests that further diagnostic tests for fetal aneuploidy are advisable for the pregnant patient, such as invasive prenatal diagnostic tests.

Cell-free DNA in a maternal test sample may contain a mixture of maternal and fetal DNA. Because surviving aneuploid individuals typically have obvious phenotypic abnormalities, in some embodiments, phenotypically normal pregnant women are presumed to be euploid. Thus, abnormalities in chromosomal representation as suggested by the present data can be reasonably attributed to abnormalities in the fetal genome.

Accordingly, in some embodiments, the Z-score is used as an indicative parameter for detecting aneuploidy in the fetal genome. In various embodiments, the abnormality can be chromosomal trisomy or monosomy, or a partial chromosomal duplication or deletion. In some embodiments, the fetus can be chromosomal mosaicism. In some embodiments, the fetal genome can have one or more chromosome translocations.

Particularly, in some embodiments, a Z-score>4 in indicates the presence of some kind of genetic abnormality in the fetal genome. In some embodiments, a Z-score>4 indicates a high risk of fetal chromosomal trisomy. In some embodiments, a Z-score>3 but <8 suggests that further diagnostic tests for fetal aneuploidy are advisable for the pregnant patient, such as invasive prenatal diagnostic tests. In some embodiments, a Z-score≥8 indicates the presence of some kind of aneuploidy in the fetal genome. In some embodiments, a Z-score≥8 indicates a high risk of fetal chromosomal trisomy. In some embodiments, a Z-score≥8 suggests that further diagnostic tests for fetal aneuploidy are advisable for the pregnant patient, such as invasive prenatal diagnostic tests.

Thus, it can be appreciated that the present methods provide an effective option for detecting fetal aneuploidies, such as trisomy or monosomy for high risk pregnancies. Particularly, fetal aneuploidies that can be detected with the present methods include but are not limited to human trisomy 13, trisomy 18, trisomy 21, and sex chromosome abnormalities.

Particularly, in some embodiments, the present NIPS methods provide improved positive predictive values (PPVs) as compared to traditional methods, such as maternal serum screening or nuchal translucency testing. More particularly, in various embodiments, the PPV of the present method can be at least 30%, 35%, 40%, 45%, 50%, 55%, 60%, 65%, 70%, 75%, 80%, 85%, 90%, or 95% for trisomy 21, trisomy 18 and/or trisomy 13. Particularly, in some embodiments, the PPV of the present method is at least 94% for trisomy 21, at least 72% for trisomy 18 and at least 39% for trisomy 13.

In some embodiments, the present method of NIPS methods further take into consideration that chromosomes may vary in composition and size from person to person due to the presence of relatively minor variations in the individual's genome. These minor variations may or may not produce any observable phenotype in a pregnant individual, but might affect diagnosis of fetal aneuploidy through a noninvasive method.

Accordingly, in one aspect, the present methods further provide a mechanism for distinguishing fetal aneuploidies from maternal chromosome variations, such as maternal copy number variations, microduplications, or microdeletions. Some maternal chromosome variations may be global, affecting multiple or all chromosomes in the maternal genome. Alternatively, some maternal chromosome variations may be local and relates to a particular chromosome in the maternal genome.

Particularly, maternal global copy number abnormalities may affect multiple chromosomes at the same time, while cases of a fetus having multiple chromosomal aneuploidies tend to be rare. Accordingly, in some embodiments, the present methods provide a mechanism that serves to examine the fetal genome karyotype by examining multiple or all chromosomes in the fetal genome. Particularly, in some embodiments, chromosomal representation values are obtained for one or more chromosomes in a sample, and are compared to corresponding reference values, such as expected normal values as estimated from presumably unaffected pregnancies. In some embodiments, a chromosome-specific Z-score is calculated for one or more chromosomes. Particularly, in some embodiments, the one or more chromosomes under examination by the present methods include at least one chromosome other than a chromosome of interest that has been previously diagnosed to be affected by aneuploidy. In some embodiments, the one or more chromosomes under examination include all chromosomes in the fetal genome.

In some embodiments, the present methods can recognize maternal contribution and exclude a detection as false-positive, when the data suggest that multiple fetal chromosomes including or in addition to the chromosome of interest are simultaneously affected by aneuploidy. Particularly, in some embodiments, a chromosome-specific Z-score is calculated for each of the multiple chromosomes. Particularly, in some embodiments, the present methods exclude detection as false-positive when multiple chromosome-specific Z-scores are above 4 in a sample. Particularly, in some embodiments, the present methods exclude a detection as false-positive when multiple chromosome-specific Z-scores no less than 8 in a sample.

Certain maternal chromosome variations, such as microduplications or microdeletions, affect only to a limited region of a chromosome, while fetal aneuploidies usually affect an entire chromosome or a substantial portion thereof. Thus, additionally or alternatively, in some embodiments, the present methods provide a mechanism that serves to distinguish fetal aneuploidies from maternal contribution by pinpointing the source of observed genetic variations to a discrete chromosomal region or regions.

Particularly, in some embodiments, the present methods can detect aneuploidy of a chromosome of interest when an observed genetic variation is consistent across the entire chromosome or a substantial portion thereof. Additionally or alternatively, in other embodiments, the present methods can exclude a detection of aneuploidy of a chromosome of interest as false-positive, when the observed genetic variation only originates from one or more regions that represent less than a substantial portion of the chromosome of interest.

Particularly, in some embodiments, the present methods analyze whether bin-specific test parameters of bins residing on the chromosome of interest are consistent across the entire or a substantial portion of the chromosome. In some embodiments, an ideogram for the chromosome of interest is generated by plotting the set of bin-specific test parameters versus the corresponding bins' chromosomal location. In some embodiments, the present methods detect aneuploidy of a chromosome of interest if the ideogram exhibit consistent bin-specific test parameters across the entire chromosome of interest of a substantial portion thereof.

In some embodiments, a bin-specific test parameter is calculated for each bin based on the total number of sequence reads aligned to the bin. In some embodiments, the bin-specific test parameter is a normalized bin read count obtained by processing a corresponding raw bin read count via one or more normalization steps as described above.

In some embodiments, the substantial portion of the chromosome of interest represents about more than about 2%, 5%, 10%, 20%, 30%, 40%, 50%, 60%, 70%, 80%, or 90% of a chromosome of interest. In some embodiments, consistency indicates that difference, if any, among the set of bin-specific test parameters is statistically insignificant. In other embodiments, consistency indicates that any difference among the set of bin-specific test parameters is less than 5%, 10% or 20%. In yet other embodiments, whether a set of bin-specific test parameters is consistent is determined as follows: (a) defining a residual as the difference between a bin-specific test parameter for a particular bin and the mean or median of all bin-specific test parameters for a chromosome of interest; and (b) calculating a standard deviation of such residues. Particularly, in some embodiments, if a standard deviation of such residues is less than 0.15, then the set of bin-specific test parameters is determined to be consistent. In some embodiments, if all the residues are within 1, 2 or 3 folds of the standard deviation, the set of bin-specific test parameters is determined to be consistent. In some embodiments, if all the residues are within ±0.15, ±0.3 or ±0.45 unit away from the mean or median, the set of bin-specific test parameters is determined to be consistent In some embodiments, maternal microduplication or microdeletion is detected, when the ideogram exhibits a large-scale difference of bin-specific test parameter in a small chromosomal region as compared to remaining regions of the chromosome. Particularly, in some embodiments, the large-scale difference means at least 1.2 fold, at least 1.5 fold, at least 2 fold, at least 2.5 fold, at least 3 fold, at least 3.5 fold, at least 4 fold, at least 4.5 fold, at least 5 fold, at least 5.5 fold, at least 6 fold, at least 6.5 fold or at least 7 fold of increase or decrease of bin-specific test parameters of certain region compared to those of other regions.

In some embodiments, a large-scale difference is defined as follows: (a) defining a residual as the difference between a bin-specific test parameter for a particular bin and the mean or median of all bin-specific test parameters for the chromosome of interest; and (b) calculating a standard deviation of such residues. Particularly, in some embodiments, a residue greater than 1, 2 or 3 folds of the standard deviation is defined to be a large-scale difference. In some embodiments, a residue more than ±0.15, ±0.3 or ±0.45 unit away from the mean or median is defined to be a large-scale difference. In some embodiments, maternal contribution is detected when the ideogram exhibits a large-scale difference of bin-specific test parameter in at least one bin of the chromosome.

In some embodiments, fetal aneuploidy is confirmed when the ideogram exhibits a small-scale increase in bin-specific test parameters compared to the normal value. Particularly, in some embodiment, the normal value is estimated based on a random set of unaffected pregnancies. Particularly, in some embodiments, a small-scale increase means that the bin-specific test parameter is increased less than 1.5 fold, less than 1.4 fold, less than 1.3 fold, less than 1.2 fold, less than 1.15 fold, or less than 1.1 fold compared to the normal value. Further, in some embodiments, the observed small-scale increase is consistent across the whole chromosome of interest, or a substantial portion thereof. Particularly, in some embodiments, the substantial portion of the chromosome of interest represents about more than about 2%, 5%, 10%, 20%, 30%, 40%, 50%, 60%, 70%, 80%, or 90% of a chromosome of interest. In some embodiments, consistency indicates that difference, if any, among the set of bin-specific test parameters is statistically insignificant. In other embodiments, consistency indicates that any difference among the set of bin-specific test parameters is less than 5%, 10% or 20%. In yet other embodiments, whether a set of bin-specific test parameters is consistent is determined as follows: (a) defining a residual as the difference between a bin-specific test parameter for a particular bin and the mean or median of all bin-specific test parameters for a chromosome of interest; and (b) calculating a standard deviation of such residues. Particularly, in some embodiments, if a standard deviation of such residues is less than 0.15, then the set of bin-specific test parameters is determined to be consistent. In some embodiments, if all the residues are within 1, 2 or 3 folds of the standard deviation, the set of bin-specific test parameters is determined to be consistent. In some embodiments, if all the residues are within ±0.15, ±0.3 or ±0.45 unit away from the mean or median, the set of bin-specific test parameters is determined to be consistent.

In one aspect, provided herein are methods for improving the positive predictive value of a non-invasive prenatal test. Particularly, in some embodiments, a maternal test sample is obtained from a pregnant woman carrying a fetus that has been previously diagnosed to be aneuploid for one or more chromosome of interest. In some embodiments, cell-free DNA contained in the maternal test sample is sequenced to produce sequence reads. In some embodiments, the sequence reads are aligned to various bins residing on one or more chromosomes of a reference genome.

In some embodiments, a bin-specific test parameter is calculated for each bin based on the total number of sequence reads aligned to the bin. In some embodiments, the bin-specific test parameter is a normalized bin read count obtained by processing a corresponding raw bin read count via one or more normalization steps as described above.

In some embodiments, a chromosome-specific Z-score is calculated for at least one confirming chromosome that is different from the chromosome of interest. In some embodiments, the method excludes the previous diagnosis as false positive, when the Z-score for the at least one confirming chromosome is great than 4. In some embodiments, the method excludes the previous diagnosis as false positive, when the Z-score for the at least one confirming chromosome is no less than 8.

Additionally or alternatively, in some embodiments, the set of bin-specific test parameters for corresponding bins that reside on a chromosome of interest are analyzed to determine whether the set of bin-specific test parameters are consistent across the entire chromosome of interest or a substantial portion thereof. Particularly, in some embodiments, an ideogram for the chromosome of interest is constructed by plotting the set of bin-specific test parameters versus the corresponding bins' location on the chromosome. In some embodiments, the present methods exclude the previous diagnosis as false-positive if the ideogram exhibit that the bin-specific test parameters are not consistent across a substantial portion of the chromosome of interest.

Particularly, in some embodiments, the substantial portion of the chromosome of interest represents more than about 2%, 5%, 10%, 20%, 30%, 40%, 50%, 60%, 70%, 80%, or 90% of a chromosome of interest. In some embodiments, consistency indicates that difference, if any, among the set of bin-specific test parameters is statistically insignificant. In other embodiments, consistency indicates that any difference among the set of bin-specific test parameters is less than 5%, 10% or 20%.

In yet other embodiments, whether a set of bin-specific test parameters is consistent is determined as follows: (a) defining a residual as the difference between a bin-specific test parameter for a particular bin and the mean or median of all bin-specific test parameters for a chromosome of interest; and (b) calculating a standard deviation of such residues. Particularly, in some embodiments, if a standard deviation of such residues is less than 0.15, then the set of bin-specific test parameters is determined to be consistent. In some embodiments, if all the residues are within 1, 2 or 3 folds of the standard deviation, the set of bin-specific test parameters is determined to be consistent. In some embodiments, if all the residues are within ±0.15, ±0.3 or ±0.45 unit away from the mean or median, the set of bin-specific test parameters is determined to be consistent.

Thus, it can now be appreciated that the present disclosure provides methods for excluding a previously diagnosed fetal aneuploidy as false-positive, thus improving the positive predictive value (PPV) of the previous test. Particularly, in some embodiments, the previously test for fetal aneuploidy can be performed through the methods presently disclosed. In other embodiments, the previously test of fetal aneuploidy can be through other methods currently available in the field or to be developed in the future. Exemplary methods for detecting fetal aneuploidy that can be used in connection with the present methods include, but are not limited to, ultra-sonographic diagnosis, amniocentesis, and conventional first or second trimester screenings for biomarkers contained in maternal serum. In some embodiments, the present method can improve the positive predicative value of a NIPS method by at least 4%, 10%, 20%, 30%, 40% and 50% for trisomy 21, trisomy 18 and/or trisomy 13. In some embodiments, the present method can improve the positive predicative value of a NIPS method by at least 4% for trisomy 21, and particularly at least 5%, for trisomy 21. In some embodiments, the present method can improve the positive predicative value of a NIPS method by at least 20%, and particularly at least 28%, for trisomy 18. In some embodiments, the present method can improve the positive predicative value of a NIPS method by at least 25%, and particularly at least 30% for trisomy 13.

In some embodiments, next-generation sequencing (NGS) methods are used, including a number of different modern high-throughput sequencing technologies. In some embodiments, sequencing methods capable of generating large numbers of bin counts are preferred, since the fetal fraction of cell-free DNA is usually low, and the excess or deficit in the assigned DNA fragments is small. In some embodiments, shotgun (genome wide) massively parallel sequencing (s-MPS) is used. In some embodiments, s-MPS relies on identification and counting of large numbers of DNA fragments in maternal specimens. Particularly, in some embodiments, millions of genome-wide fetal and maternal fragments are simultaneously sequenced and informative sequences are mapped to discrete locations on all chromosomes. Thus, for example, if fetal trisomy is present, there will be a relative excess of counts for a given chromosome and with a monosomy deficit.

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, CA) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454TM GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added poly-A tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA and HiSeq 2000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

Certain sequencing methods produce result that is biased by the varying guanine-cytosine (G-C) base content of the sequence. Accordingly, in some embodiments, GC-sequencing biases are corrected during data processing. According to the present disclosure, various methods for correcting GC-sequencing biases can be used in connection with the present methods. An exemplary procedure is provided in the example section below. A skilled artisan would be able to identify other suitable methods, either readily available in the field or to be developed in the future.

EXAMPLES

Example 1: Assay Development

The following sections describe materials and methods used for performing the present NIPS assay.

1. Patient Sample Collection

In one example, for assay development, verification, and validation studies, applicant obtained samples from pregnant women from Sequenom (San Diego, CA), Precision Medicine, and consented volunteers. For singleton pregnancies Applicants obtained 3,750 samples from Sequenom, 165 from Precision Medicine, and 10 from volunteers; Sequenom also provided samples from 115 twin gestations. The Sequenom samples were scheduled to be discarded and were de-identified before being sent to Applicants. The samples from Precision Medicine were consented using their protocols. Volunteers provided written informed consent via signed forms approved by the Western Institutional Review Board, which specifically reviewed and approved this study. The study was conducted according to the principles in the Declaration of Helsinki.

2: Next-Generation Sequencing

In one example, whole blood was collected in two, 10 mL Cell-Free DNA BCT blood collection tubes (Streck, Omaha, NE), and transported at room temperature. Blood tubes were processed within 4 days of draw. The plasma was isolated from each of these samples using a Tecan EVO 200 liquid handler (Tecan, Mannedorf, Switzerland). The Tecan EVO 200 liquid handler performs the following activities: centrifuges the Streck blood tubes at 22° C. for 10 minutes at 2,500×g, transfers the plasma to a 15 mL conical tube, centrifuges the 15 mL conical tube at 22° C. for 20 minutes at 3,200×g, transfers plasma to a final 15 mL conical tube. The cell-free DNA (cfDNA) is then extracted from 4 mL of plasma using DynaMax chemistry (Thermo Fisher Scientific, Waltham, MA), following manufacturers recommendations, with the aid of a Kingfisher Flex Purification System (Thermo Fisher Scientific). cfDNA was made into sequencing ready libraries using the NEBNext® Ultra™ DNA Library Prep Kit for Illumina® (New England Bio-Labs Inc, Ipswich, MA) following manufacturers recommendations. During PCR, a 10 bp barcode is amplified onto each sample using the reverse PCR primer, all reactions shared a common forward primer. The universal forward primer sequence was:

(SEQ ID NO: 1)
AATGATACGGCGACCACCGAGATCTACACTCTTTCCCTACACGACGCT

CTTCCGATCT;

The reverse primer was:

(SEQ ID NO: 2)
CAAGCAGAAGACGGCATACGAGATXXXXXXXXXXGTGACTGGAGTTCA

GACGTGTGCTCTTCCGATCT, where X denotes the 10 base barcode location. PCR was performed on a SimpliAmp Thermal Cycler (Thermo Fisher Scientific). PCR conditions were as follows: initial denaturation at 98° C. for 30 seconds, 10 cycles of denaturation at 98° C. for 10 seconds, annealing at 65° C. for 30 seconds and extension at 72° C. for 30 seconds, final extension at 72° C. for 5 minutes, and ends with a 4° C. hold. Following PCR, the products were purified using the Agencourt AMPure XP PCR Purification beads (Beckman Coulter, Brea, CA) following manufacturers recommendations. The AMPure bead to PCR product ratio was 1:1. The cleaned-up PCR products were quantified using the Quant-It PicoGreen dsNDA Assay Kit (Thermo Fisher Scientific), following manufacturer's recommendations, and read on an Infinate 200 PRO Microplate Reader (Tecan). Samples were normalized to 2 nM, and pooled with 12 samples in each library. Library pools were denatured and further diluted to 15 pM. A 5% PhiX Control (Illumina, San Diego, CA), was spiked into each pool. The pooled libraries were clonally amplified and bound to high output flow cells (Illumina) using the cBot system from Illumina. Sequencing was performed on a HiSeq2500 system by single read 36 cycles followed by 10 cycles to sequence the index. A minimum of 9 million reads were required for the bioinformatics process. Data were streamed from the Hi Seq2500 system to an Isilon (EMC Isilon, Seattle, WA) server, where the data analysis pipeline was begun automatically.

Applicants used a read length of 36 base pairs in one direction at an average sequencing depth of 0.6×. All quality score "Q scores" were >30.

3: Fetal Fraction Estimations

In some embodiments, fetal fractions (FF) were calculated based on X chromosome under representation or Y chromosome over representation using the following methods.

a) Fetal fraction was estimated as $2 \times (1 - \bar{N}_{23}/\bar{N})$, where $\bar{N}_{23}/\bar{N}$ is average read count per bin for chromosome X normalized to the autosome bin average. b) Applicant used R package RAPIDR based on X chromosome under representation to estimate male FF based on X chromosome under representation. c) FF was estimated based on X chromosome under representation with non-pregnant female as two X chromosome copy reference, non-pregnant male as single X chromosome copy reference and known FF samples as standard controls. d) FF was estimated based on Y chromosome over representation with non-pregnant female as Y chromosome absence (0% Y) reference, non-pregnant male as Y chromosome presence (100% Y) reference and known FF samples as standard controls. For better male FF estimation the median value of these four calculations was used as our final male FF and such median of four FF is correlated very well with a set of known FF sample shaving R square=0.9752 with y-intercept=0.

For female fetuses, fetal fraction was estimated using a regularized regression model. Briefly, a training set of 3281 samples from known male fetuses was used to model fetal fraction (estimated as described above) as a function of sample bin counts normalized by the sample total read count but uncorrected for GC content. Bins residing on chromosomes 13, 18, 21, X or Y chromosomes were excluded from the modeling process. The model was a regularized linear regression model implemented with the R package "glmnet" (version 1.9-8). Ten-fold cross-validation using an alpha parameter of 1 was used to select the lambda parameter having the minimum cross-validated error for use in building the final model which is subsequently used to estimate fetal fraction for female fetuses.

Fetal fractions were calculated for male fetuses using Y chromosome-specific sequences. For female fetuses Applicants developed a proprietary bioinformatics approach.

4: GC Correction

Certain genomic regions (e.g., Chromosomes 13 and 18) are GC-rich relative to others, causing sequencing bias that may skew the percentage of counts mapped to those chromosomes. Therefore, in some embodiments, GC correction is performed to reduce variability due to sample differences with respect to the magnitude of relationship between GC content and observed read counts.

Particularly, GC content for regions corresponding to the genomic locations of sequenced bins were obtained from the HG19 reference genome materials at UCSC Genome Browser (https://genome.ucsc.edu/). Then GC content was discretized by rounding GC content values to 3 decimal places such that multiple bins correspond to each unique value of GC content. The median of scaled (by total autosome read count) autosomal bin counts were determined at each unique level of GC content. Then, local polynomial regression (loess) is performed to estimate bin count as a smooth function of GC content. Finally, the GC normalized bin count is calculated as the median of the scaled autosomal read count plus the difference (residual) of the observed read count and the read count predicted by the loess regression model.

5: Calculation of Chromosome-Specific Z-Scores

In some embodiments, a chromosome-specific Z-score is calculated for each chromosome of interest. Particularly, bin read count (RC) data were first scaled (divided) by its own sample autosomal total read counts. Then GC correction was performed using local polynomial regression fitting R loess function and hg19 data (see Example 3). A pca model was applied to such normalized data to remove high order artifacts. Particularly, high order artifacts were subtracted as defined by a regression of normalized bin counts of sample vs. 1st 10 principal components among the normalized bin read counts determined from a reference population of presumably unaffected samples.

Then, a chromosome representations was calculated as the sum of normalized individual bin read counts that reside on the chromosome of interest scaled (divided) by the sum of all autosomal normalized individual bin read counts, and particularly $$chrRep_i = \frac{chrTotalRC_i}{\sum_{j=1\ ...\ 22} chrTotalRC_j}$$

$chrTotalRC_i$: sum of normalized individual bin read counts that reside on the chromosome of interest; and $\Sigma_{j=1\ ...\ 22}chrTotalRC_j$: sum of all autosomal normalized individual bin read counts (chromosomes 1 through 22).

Then, each chromosome specific Z-score was calculated as $$Z = \frac{x - \mu}{\sigma}$$

x: sample chromosome representation ($chrRep_i$);

μ: chromosome representation plate median (i.e., the median of the chromosome representation values among all samples on the plate on which the sample of interest was run); and σ: chromosome representation median absolute deviation (MAD), as calculated using a reference set of 5406 samples of presumably unaffected samples.

6: Generation of Chromosomal Ideograms

In some embodiments, an ideogram is generated for a chromosome of interest. Particularly, raw bin read count (RC) data were first scaled (divided) by its own sample's autosomal total read counts. Then GC correction was performed using local polynomial regression fitting R loess function and hg19 data (see Example 3). Then the data was centered at the median of scaled autosomal bin read counts. Then, the data was further scaled (multiplied) by total number of bins. Each bin count was then scaled (divided) by median of corresponding normalized bin count from a reference population of presumably unaffected samples. The data was then centered around 1 and corrected (subtracted) by median of sample's normalized autosomal bin counts. High order artifacts were subtracted as defined by a regression of normalized bin counts of sample vs. 1st 10 principal components among the normalized bin read counts determined from a reference population of presumably unaffected samples. Finally, the resulting normalized bin read counts were plotted versus the chromosomal location of corresponding bins to obtain the chromosomal ideogram.

7: Clinical Confirmation of NIPS Result

Follow-up information was obtained for every positive NIPS result obtained through clinical testing at a reference laboratory. A genetic counseling team contacts the referring physician to determine the outcome of the pregnancy.

Example 2: Assay Verification and Validation

Once the performance parameters of the assay were established, a series of verification samples including known unaffected and known aneuploid pregnancies were tested. This series of 2,085 samples included trisomy 21 (n=69), trisomy 18 (n=20), and trisomy 13 (n=17). No unaffected pregnancy had a Z-score>4 and no affected pregnancy had a Z-score<8. Following assay verification, a validation set comprising 552 samples was analyzed, including samples known to be positive for trisomy 21 (n=21), trisomy 18 (n=10), trisomy 13 (n=1), and XO (n=1). Once again, no unaffected pregnancy had a Z-score>4 and no affected pregnancy had a Z-score<8.

Since there was no difference in performance between the verification and validation studies, the results were combined for analysis. The effects of GC correction were least for chromosome 21, which has normal GC content, intermediate for chromosome 18, known for having an intermediate increase and GC content, and greatest for chromosome 13, which has the highest GC content (FIG. 1). Using raw data, a Z-score threshold of 4 yielded absolute discrimination between the 2,498 unaffected pregnancies and the 90 trisomy 21 samples; no unaffected pregnancy had a Z-score>4, and no affected pregnancy had a Z-score<8. However, GC correction improved discrimination for chromosomes 13 and 18: without GC correction, most trisomy 13 samples had Z-scores less than 4; after GC correction, all trisomy 13 samples had Z-scores well over 8. GC correction also allowed complete discrimination of trisomy 18 from unaffected pregnancies. Therefore, after GC correction and biostatistical smoothing, the assay provided 100% discrimination between affected and unaffected pregnancies (FIG. 1, right panel) demonstrates the combination of GC correction with statistical smoothing, which further improves assay performance.

Also analyzed was a series of 115 samples from twin gestations with known aneuploidy status as part of assay validation, including 10 trisomy 21, 4 trisomy 18, and 13 trisomy 13 samples. Following GC correction and smoothing, all samples with autosomal trisomies had Z-scores>11 and all unaffected pregnancies had Z-scores<4. Overall, discrimination was greater in twin than singleton samples (data not shown), even though most twins would be expected to be discordant for autosomal trisomies.

As a final validation for trisomy detection, samples were obtained from 100 consented volunteer pregnant women and split the samples between our laboratory and Sequenom. Results were concordant in all cases. This series had 99

24

Based on the above validation and verification results, for clinical implementation a Z-score cutoff of ≤4 was used for unaffected pregnancies and >8 for affected pregnancies. Z-scores>3 but <8 prompted further examination. Review of the first 10,000 clinical samples revealed abnormal NIPS results in 180 (1.8%) (Table 1). Overall positive rates were 1.0% for trisomy 21, 0.36% for trisomy 18, 0.21% for trisomy 13, and 0.17% for sex aneuploidies. One sample was positive for the DiGeorge microdeletion and 2 cases had 2 abnormalities. Of the first 10,713 samples tested, results could not be reported in 94 (0.88%); the cause was low fetal fraction in 63 cases (0.59%) and uninformative DNA pattern, failure to meet quality metrics, or other technical issues in 31 samples (0.29%).

TABLE 1

Follow-up of Clinical Samples Positive for Fetal Aneuploidies on Non-invasive Prenatal Screening

| Positive NIPS Result | Number singleton (twin) | Confirmation of Positive NIPS Result | | No Follow-up Testing | | | | Follow-up pending | Lost to follow-up | PPV, % | Adjusted PPV^a, % |
|---|---|---|---|---|---|---|---|---|---|---|---|
| | | Karyo-type | U/S or physical exam | SAB (twins) | Follow-up ongoing | Pregnancy Terminated | False+ | | | | |
| T21 | 99 (4) | 37 (3) | 1 | 7 (1) | 26 | 11 | 1[b] | 10 | 6 | 98 | 100 |
| T18 | 35 (1) | 14 | 9 | 1 | 4 | 0 | 2[c] | 4 | 2 | 92 | 96 |
| T13 | 20 (1) | 7 | 2 | 2 | 2 | 0 | 4[d] | 3 | 1 | 69 | NA |
| 45, X | 9 | 3 | 3 | 0 | 0 | 0 | 1[e] | 2 | 0 | 86 | 100 |
| 47, XXX | 5 | 2 | 0 | 0 | 1 | 0 | 1 | 1 | 0 | 67 | NA |
| 47, XXY | 2 | 1 | 0 | 0 | 1 | 0 | 0 | 0 | 0 | 100 | NA |
| 47, XYY | 1 | 0 | 0 | 0 | 1 | 0 | 0 | 0 | 0 | NA | NA |
| 22q del | 1 | 1 | 0 | 0 | 0 | 0 | 0 | 0 | 0 | 100 | NA |
| T21 & 45, X | 1 | 0 | 0 | 1 | 0 | 0 | 0 | 0 | 0 | NA | NA |
| T21 & T13 | 1 | 0 | 0 | 0 | 0 | 0 | 0 | 1 | 0 | NA | NA |

[a]PVV excluding false-positives reclassified as true negatives based on changes in reporting rules.
[b]Re-evaluation of data showed multiple chromosome variations.
[c]Twin gestation with one twin having mass felt to be teratoma
[d]1 patient with significant fibroids.
[e]Maternal 45, X/46, XX.

unaffected and 1 sample predicted to be from a woman carrying a fetus with trisomy 21 by both laboratories.

To assess the accuracy of the NIPS assay for fetal sex determination, 372 (188 male) samples were tested over the course of 6 different assay setups. Fetal sex had been previously determined using the Sequenom Maternity21 Plus assay, but was not phenotypically confirmed. The current NIPS assay yielded concordant results in all but 1 sample, in which results indicated a male fetus when a female fetus was expected. Thus, overall accuracy was 99.7% (371/372). However, the fetal fraction for this sample (2.75%) was below the 5% threshold for reporting (not shown) and would have prompted a request for a new sample in clinical testing.

The above data indicate that the present NIPS assay is verified and validated for clinical implementation.

Example 3: Clinical Implementations

The following sections describes results of the present NIPS assay in exemplary clinical implementations. Particularly, samples beginning at the 10$^{th}$ gestational week were accepted. Greater than 90% of samples received are from between the 10$^{th}$ and 15$^{th}$ gestation week.

1: Maternal Microduplication

NIPS was performed using whole genome shotgun sequencing (a method that involves sequencing fragments of DNA that, in the aggregate, represent almost all of the genome). This allows the generation of a karyogram that graphically represents Z-scores throughout the entire genome. Snyder et al. described two cases of falsely positive NIPS results for Trisomy 18 that were later found to be the result of maternal microduplications of chromosome 18. Copy-number variation and false positive prenatal aneuploidy screening results. N. Engl. J. Med. 2015; 372(17): 1639-1645. Thus a process was instituted in which, for every positive result obtained by NIPS, the karyogram of the affected chromosome was generated and examined. For a true positive result, sequence reads are increased throughout the entire chromosome. When a maternal microduplication is present, only a small region (i.e., the region that is duplicated) of the chromosome is represented through an increased number of sequence reads. The process was able to identify, in a series of 31,278 screened pregnant women, 61 women in whom maternal microduplications occurring on chromosomes 13, 18, and 21 yielded false positive results.

Until Applicant was confident that karyograms correctly predicted maternal microduplications, suspected microduplications were confirmed by microarray analysis (Affymetrix CytoScan® HD). Subsequently, maternal microarray analysis was performed at the discretion of the ordering physician. A genetic counselor contacted the physician with the report, which included a description of the suspected maternal microduplication and an offer of confirmatory microarray analysis (at no charge for under-insured patients).

Figure 2:
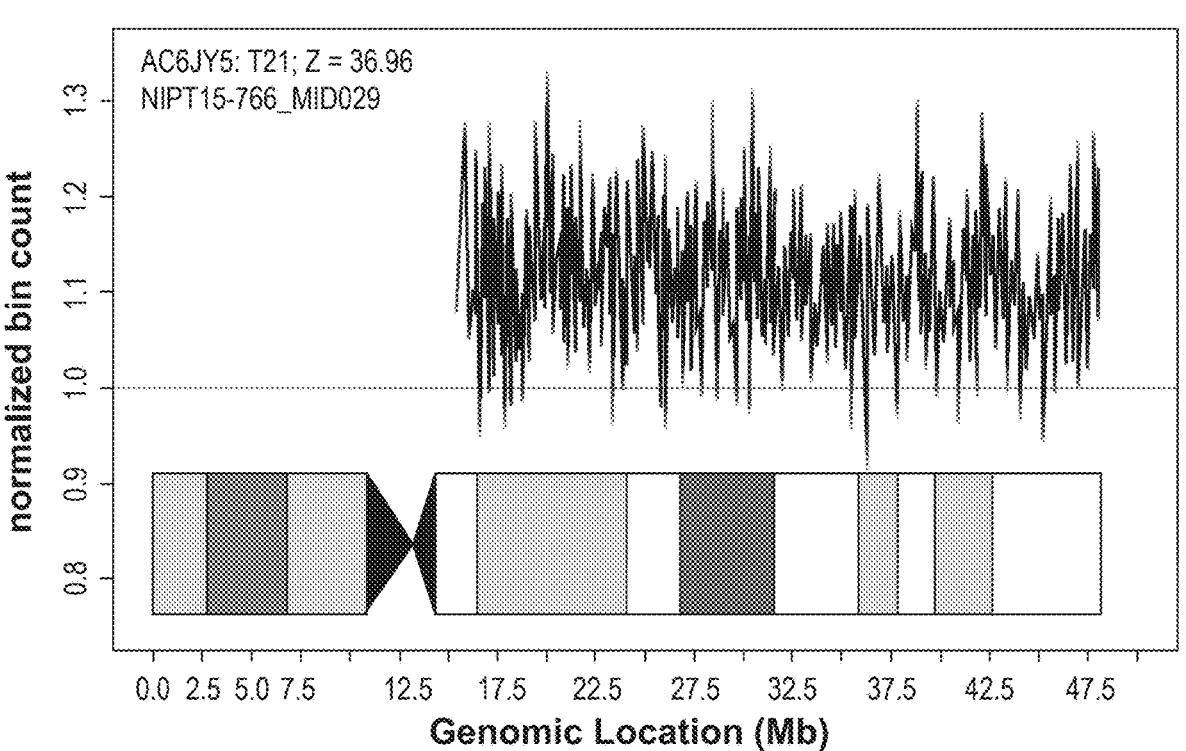
FIG. 2 shows an ideogram for chromosome 21 constructed using a prenatal sample positive for trisomy 21. Each point represents a normalized count for a particular bin on a particular chromosome; an euploid value on the Y axis is 1.0. As shown in the figure, the entire chromosome 21 demonstrated duplicated material. The Z-score for this sample was 36.96.
Figure 3:
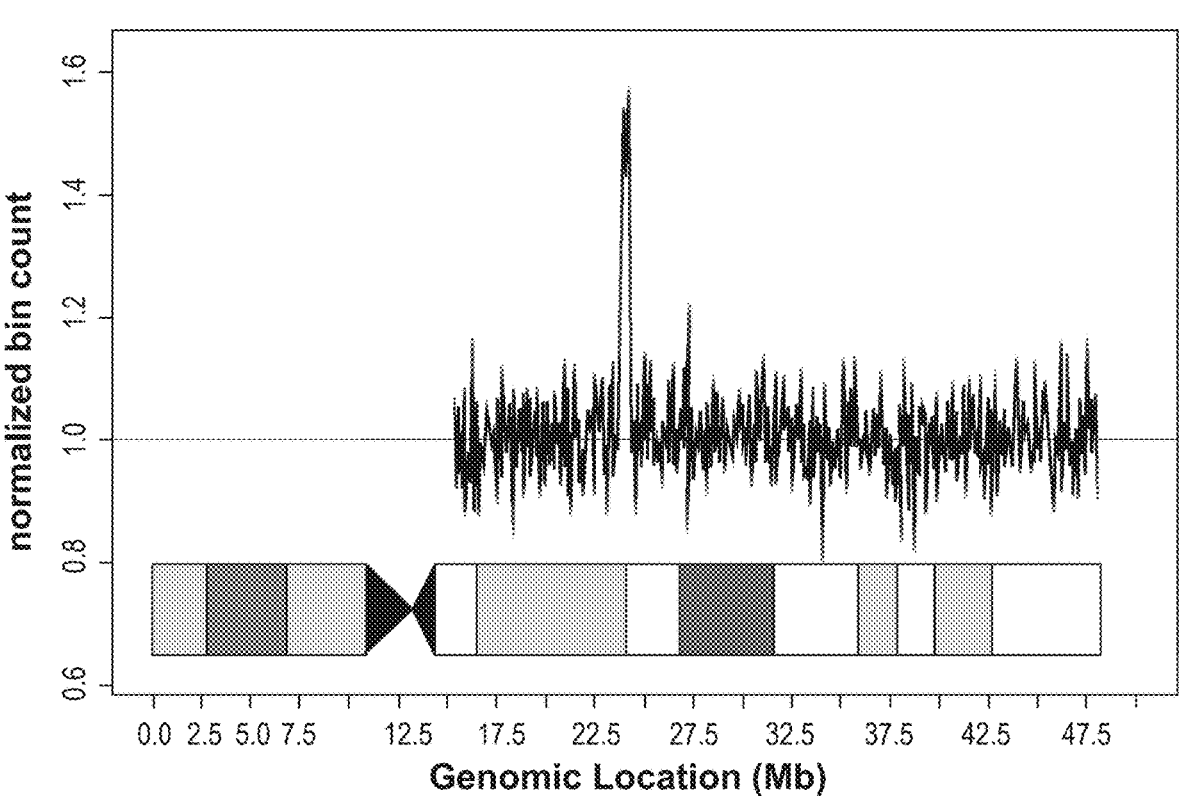
FIG. 3 shows an ideogram for chromosome 21 from a patient with a maternal microduplication.
Figure 4:
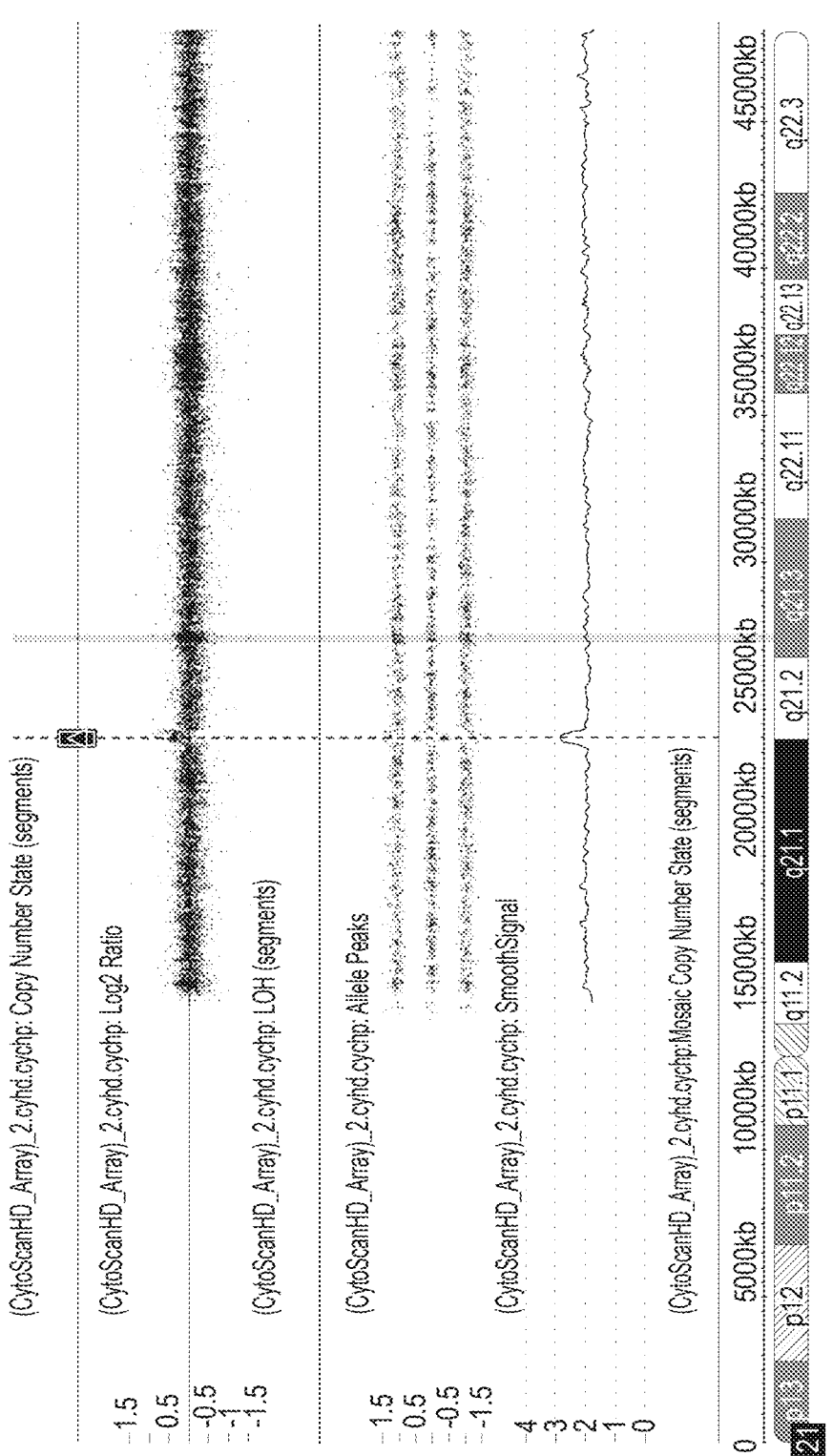
FIG. 4 shows microarray data for maternal DNA for the patient in FIG. 3.
Figure 5:
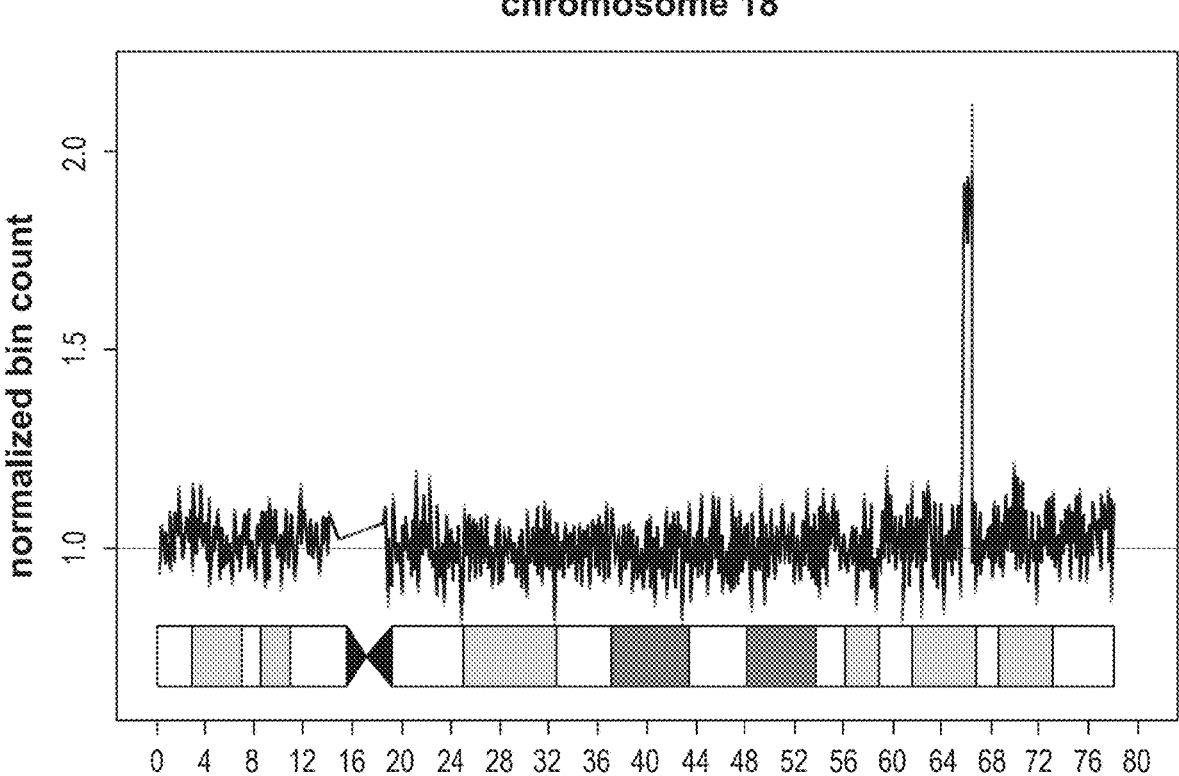
FIG. 5 shows an ideogram for chromosome 18 from a patient with a maternal microduplication.
Figure 6:
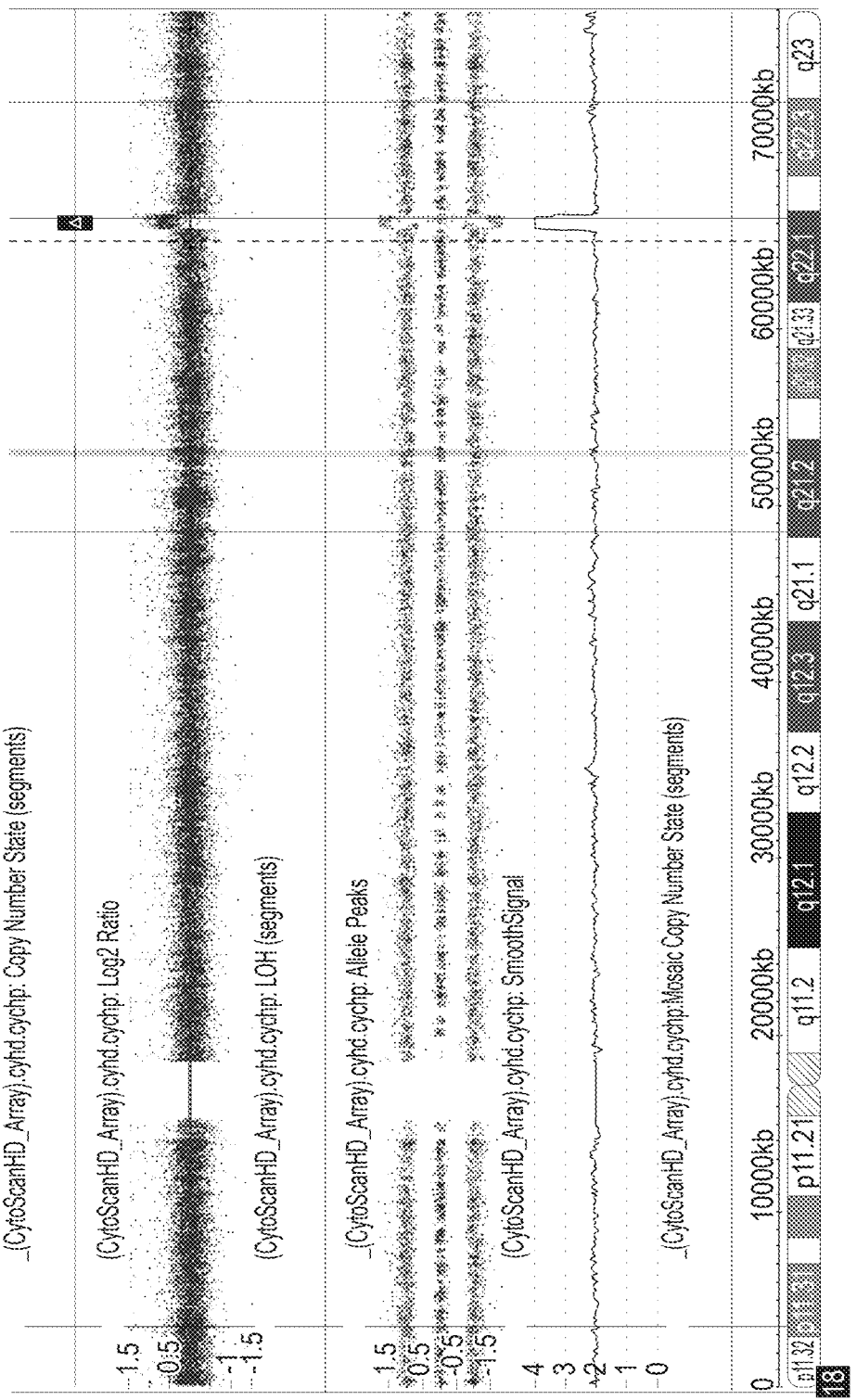
FIG. 6 shows microarray data for maternal DNA for the patient in FIG. 5.

For example, early during clinical testing 2 cases with intermediate Z-scores between 3 and 8 were encountered. One had a Z-score of 5.11 for trisomy 21 and another had a Z-score of 6.93 for trisomy 18. "False-positive" NIPS results may be due to maternal microduplications and thus chromosomal ideograms were used to investigate whether these intermediate Z-scores represented maternal microduplications. FIG. 2 shows the ideogram for a typical NIPS result from a fetus confirmed to have trisomy 21. In both of the cases, the ideograms clearly showed that the duplications were in a small portion of the affected chromosomes (FIG. 3). With permission from the ordering physicians, microarray analysis was performed on the maternal buffy coat cells, which confirmed the maternal microduplication on chromosome 21 (FIG. 4) and 18 (FIG. 5 and FIG. 6). Henceforth, the ideogram was examined for each chromosome with an elevated Z-score before reporting an abnormal result, to ensure the entire chromosome is duplicated and the result is not due to a maternal microduplication.

Microarray analysis showed the presence of a maternal microduplication in all confirmatory tests carried out. The identification of maternal microduplications as a source of false positive results improved the PPV of our screen to 98%, 92% and 69% for Trisomies 21, 18 and 13, respectively (Table 2). True positives for Trisomy 21 were confirmed by karyotype and/or microarray analysis of amniocytes. Some true positives for Trisomies 13 and 18 were confirmed by the presence of characteristic sonographic abnormalities.

If there was no contact from delivering physician or neonatologist, it was assumed the delivery was unaffected. None of the maternal duplication births were Trisomies. There are no reported affected births with Trisomy 13 or 18, leading to a NPV of 100%. There was a single newborn with Trisomy 21, leading to an NPV of >99.9999%.

TABLE 2

Follow-up of Clinical Samples Positive for Fetal Aneuploidies on Non-invasive Prenatal Screening

| Chromosome | Positive Trisomy | Maternal Micro-duplication | Tested and Confirmed by Microarray | Improvement in PPV |
|---|---|---|---|---|
| 21 | 313 | 12 | 9 | +4% (94% – >98%) |
| 18 | 106 | 21 | 3 | +20% (72% – >92%) |
| 13 | 93 | 28 | 2 | +30% (39% – >69%) |

These results suggests that the present NIPS assay can distinguish maternal microduplications from true fetal trisomy, thus avoiding false-positive results caused by maternal duplications.

2: Maternal Global Copy Number Abnormalities

In one case, NIPS yielded a positive result for trisomy 21 with a Z-score of 21 but amniocentesis revealed a euploid fetus. The NIPS data for the entire genome were thus examined and revealed copy number changes at multiple chromosomes, reflected by elevated Z-scores for chromosomes 3, 9, and 21, and negative Z-scores ($<-8$) for chromosomes 4, 6, and 11. The mother had large fibroids. Uterine fibroids can shed DNA into the circulation, causing artificial copy number changes in NIPS analysis. Following this case, a procedure was instituted to examine the entire genome of positive NIPS cases to avoid reporting false-positive results due to global circulating aneuploidy. There have been a total of 6 samples with elevated Z-scores for chromosomes 13, 18, or 21 that have also had multiple copy number abnormalities on several other chromosomes. All microarray raw data has been uploaded to the National Center for Biotechnology Information Gene Expression Omnibus as accession number GSE84810.

These results suggest that the present NIPS assay can distinguish maternal global copy number abnormalities from true fetal trisomy, thus avoiding false-positive results caused by maternal global copy number variations.

3: Mosaicism and Translocations

There was a single case of Down syndrome with a 14:21 Robertsonian translocation. This case had a highly elevated Z-score of 30.78, which was not unexpected, since most chromosome 21 material was duplicated. Another patient had an intermediate Z-score (3.57) for chromosome 21. A second sample, submitted after consulting the physician, had a Z-score of 4.22, and a third had a Z-score of 5.57. G banding analysis of amniocytes following amniocentesis revealed mosaic trisomy 21 with 7 trisomic cells and 29 euploid cells counted. A case with a highly elevated chromosome 21 Z-score (24.43) had amniocentesis demonstrating 15 trisomic cells and 5 euploid cells. A final mosaic case had a Z-score of 8.41 for chromosome 21, and fetal mosaicism for Down syndrome was diagnosed by amniocentesis. The amniocyte karyotype was performed by another laboratory, and we could not obtain the ratio. The present NIPS assay detected a single mosaic fetus for trisomy 13 following a Z-score 10.79. This sample had a trisomy:euploid cell ratio of 16:4.

In all mosaic cases, the present NIPS analysis did not predict the mosaicism. The mosaicism was reported when follow up information on the high risk cases was obtained.

Because the percentage of trisomy mosaicism in amniocytes may not reflect the percentage in the chorion, it is difficult to estimate the analytical sensitivity of our assay for mosaic Down syndrome. However, these results suggest that the present NIPS assay can detect fetuses with as little as 25% trisomic cells.

4: Sex Chromosome Aneuploidies

Maternal genetic variations can also affected sex chromosome aneuploidy screening. In one case positive for 45,X (Turner syndrome), the estimated fetal fraction was >50% and amniocentesis revealed a euploid fetus. Maternal DNA analysis revealed maternal mosaicism for 45,X. Three other cases showed a negative fetal fraction on NIPS; all 3 women were non-mosaic for 47, XXX. Other than the single case of maternal mosaicism for Turner syndrome, all confirmed sex aneuploidies were correctly identified.

These results suggest that the present NIPS assay is able to detect fetal sex chromosome aneuploidy at least when the mother is non-mosaic.

5: Twins Cases

Four sets of twins had elevated Z-scores for trisomy 21. One pregnancy resulted in fetal demise of one twin without genetic testing. In 2 pregnancies, the diagnosis of Down syndrome was confirmed in 1 twin. In a third case, 1 twin had a teratoma and both had normal karyotypes. There was 1 twin gestation positive for trisomy 18, which miscarried without genetic testing.

Information of whether these twin gestations were either monochorionic or dichorionic was not obtained in this study. Since 80% of twin gestations are dichorionic, it was assumed that this was also the case with the present case. One might expect Z-scores for twins discordant for trisomies to be lower than from singletons, but this does not appear to be case. More data will be necessary before any conclusion can be drawn regarding the mechanism of circulating fetal DNA in twin gestations.

These results suggest that the present NIPS assay can yield similar results in twin pregnancy cases as singleton cases.

6: Positive Predictive Values (PPV) of Previously Available Methods.

A study is performed to assess positive predictive values for previously available NIPS methods. Particularly, 211 consecutive specimens were analyzed, along with combined data from more recent publications, for a total of 1547 samples in the combined data set (Table 3). The cumulative PPVs were 91% for trisomy 21, 73% for trisomy 18, 39% for trisomy 13, and 49% for sex chromosome aneuploidies. These numbers suggest that the PPV is not improving over the years for the previously available first-generation NIPS tests. Meck and colleagues recently reported similar PPV results in a series of 216 samples referred for invasive testing following NIPS (See Meck et al. Noninvasive prenatal screening for aneuploidy: positive predictive values based on cytogenetic findings. *Am J Obstet Gynecol.* 2015; 213: 214.e1-5.) These data suggest that to improve the PPV of NIPS for aneuploidies, the false-positive rate must be further decreased.

TABLE 3

Positive Predictive Values for Noninvasive Prenatal Screening Performed at Third-party Laboratories

| NIPS Result (prevalence) | Current Study[a], Number Cases | Current Study + Literature (PPV) [20, 23, 25-28] Number Cases (PPV) |
|---|---|---|
| Trisomy 21 (1:185) | 84 (85%) | 1174 (91%) |
| Trisomy 18 (1:470) | 53 (57%) | 350 (73%) |
| Trisomy 13 (1:1500) | 28 (36%) | 136 (39%) |
| Sex Aneuploidy (1:1000) | 39 (38%) | 115 (49%) |
| Microdeletions (3:000) | 13 (38%) | Not Determined |

[a]Based on results of invasive follow-up testing performed at Quest Diagnostics; NIPS performed elsewhere. The performing laboratory was known in 86 samples and included Natera (43 samples), Sequenom (20), Ariosa (16), and Verinata (7).

7: Positive Predictive Values (PPV) of the Present Methods.

Confirmation of positive NIPS results for trisomy 21 was based on invasive testing. Sonographic findings for trisomy 21 confirmation were excluded because most "soft" findings lack specificity. Accepted were invasive testing and ultrasound evidence of abnormalities as confirmation of trisomy 18 and 13, since there are clear sonographic findings in both disorders to confirm NIPS results.

In all, 103 pregnancy samples were positive for trisomy 21, including 99 singleton and 4 twin pregnancies. Of these, 87 had successful follow-up; follow-up is pending in 10 patients; and 6 were lost to follow up. Forty-two (48%) of cases with follow-up had confirmation available by invasive testing or physical examination at delivery, including 3 twin gestations (Table 1). The positive NIPS result was confirmed in all but 1 trisomy 21 case, and all twin gestations had 1 affected and 1 unaffected fetus. Thus, the PPV for trisomy 21 was 98%. The single false-positive trisomy 21 NIPS result was associated with multiple maternal genetic abnormalities (described above) and would not have been reported positive using the new reporting criteria. Therefore, with the current practices in place, the PPV for trisomy 21 would have been 100%. Because many pregnancies have no confirmation available, these data must be considered preliminary. In addition to confirmed cases, 8 pregnancies (7 singletons, 1 twin) positive for trisomy 21 on NIPS suffered spontaneous abortion (Table 1), consistent with an increased spontaneous abortion rate for aneuploid pregnancies. Eleven (13%) women with positive trisomy 21 NIPS results elected to terminate their pregnancies without confirmation by invasive testing, while 26 (30%) continued their pregnancies without invasive testing.

Of the 35 singleton and 1 twin pregnancy positive for trisomy 18, 30 had successful follow-up. Direct (invasive testing) or indirect (suspected based on ultrasound findings) confirmation of positive results was available for 25 cases (83%). All but 2 were confirmed to have trisomy 18, yielding a PPV of 92% (Table 1). One false-positive result involved the twin gestation in which 1 twin had a coccygeal mass thought to be a teratoma (described above). This case should have been excluded from NIPS given the frequent chromosomal abnormalities associated with neoplasias. Without this case, the PPV for trisomy 18 would have been 96%. Four (13%) women with positive trisomy 18 NIPS results declined further testing and are continuing their pregnancies. There was only 1 spontaneous abortion among pregnancies positive for trisomy 18.

Twenty-one samples were positive for trisomy 13, including 17 (81%) with complete follow-up: 9 were confirmed positive based on invasive testing or suspected positive based on ultrasound findings, and 4 were false-positives. Thus, the PPV for trisomy 13 was 69%. Of the 4 false-positive cases, 1 involved uterine fibroids (described above; the others remain unexplained. Placental material may be obtained to investigate the possibility of confined placental mosaicism. These cases could represent vanishing twins or confined placental mosaicism, since they had high Z-scores and no global abnormalities.

These results suggest that the positive predictive values of the present NIPS assay are at least 98% for trisomy 21, 92% for trisomy 18 and 69% for trisomy 13, which are significantly improved as compared to conventional methods.

8: Sex Chromosome Aneuploidies and Microdeletions

Of 9 samples positive for Turner syndrome (45,X) (Table 1), 7 had available follow-up data; 1 was false-positive (PPV=86%). This was the case of maternal mosaicism for Turner syndrome described above. Using the present reporting rules, this case would have been reported as suspected maternal variation because the fetal fraction was >50%. Excluding this would lead to a theoretical 100% PPV for Turner syndrome.

Figure 7:
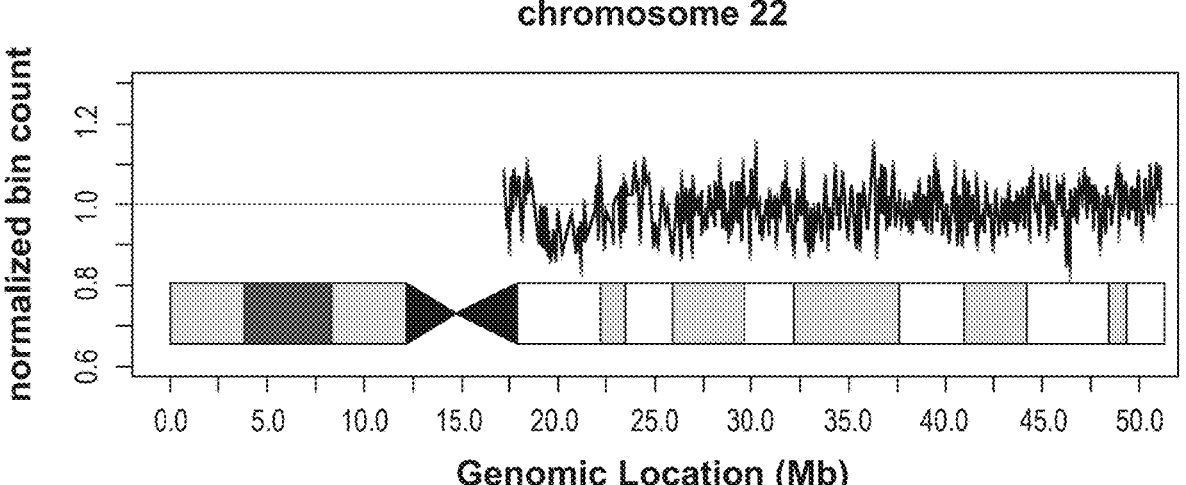
FIG. 7 shows an ideogram for chromosome 22 from a patient with a fetal microdeletion in the DiGeorge region.

Of 5 cases positive for 47,XXX, 2 have follow-up information; both were confirmed to have that karyotype. Two cases were positive for Klinefelter syndrome, and the single fetal genotype obtained confirmed the 47,XXY karyotype. Only one sample was positive for 47,XYY, but follow-up information was unavailable. Only one case involved microdeletion in the DiGeorge region of chromosome 22 (FIG. 7). The DiGeorge-specific Z-score was −7. Amniocentesis confirmed the abnormality. Two samples had 2 abnormalities: 1 with trisomy 21 and Turner syndrome that miscarried and the other with high risk for both trisomy 21 and 18, for which no follow-up data were received.

These results suggested that the present NIPS assay is able to detect sex chromosome aneuploidies and microdeletions, with a theoretical 100% PPV for Turner syndrome.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications ciently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification

---

SEQUENCE LISTING

```
<160> NUMBER OF SEQ ID NOS: 2

<210> SEQ ID NO 1
<211> LENGTH: 58
<212> TYPE: DNA
<213> ORGANISM: Artificial Sequence
<220> FEATURE:
<223> OTHER INFORMATION: Synthetic primer

<400> SEQUENCE: 1
aatgatacgg cgaccaccga gatctacact ctttccctac acgacgctct tccgatct          58

<210> SEQ ID NO 2
<211> LENGTH: 68
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (25)..(34)
<223> OTHER INFORMATION: a, c, t, g, unknown or other

<400> SEQUENCE: 2
caagcagaag acggcatacg agatnnnnnn nnnngtgact ggagttcaga cgtgtgctct          60
tccgatct                                                                  68
```

--- and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as suffi-

What is claimed is:

1. A method for detecting a false-positive diagnosis of chromosomal aneuploidy in a fetus by a non-invasive prenatal screening (NIPS), comprising:
    (a) sequencing cell-free DNA from a maternal test sample of a pregnant woman carrying the fetus to provide at least 9 million sequence reads; wherein the fetus has been diagnosed to be aneuploid of a chromosome of interest by the NIPS;
    (b) dividing a chromosome of interest diagnosed to be aneuploid into a plurality of bins, each bin having a chromosomal location, wherein each bin has a length of between 5 kb and 500 kb;
    (c) aligning the at least 9 million sequence reads to the plurality of bins;
    (d) generating a raw bin read count by counting the total number of sequence reads aligned to each of the plurality of bins;

(e) calculating a bin-specific test parameter by scaling the raw bin read count with an autosomal total read count, and performing a GC correction of the scaled bin read count to produce a GC corrected scaled bin read count;

(f) plotting the bin-specific test parameters versus the chromosomal locations of corresponding bins to produce an ideogram of the chromosome of interest; and (g) filtering confounding signals to detect the false-positive diagnosis when the ideogram exhibits an increase of a bin-specific test parameter in at least one bin compared to the mean or median of the bin-specific test parameters for the plurality of bins of the chromosome of interest, and wherein the increase is at least 1.2-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold or at least 7-fold, wherein the diagnosed chromosomal aneuploidy is confirmed by performing an amniocentesis on the pregnant woman when the filtering does not detect the false-positive diagnosis.

2. The method of claim 1, further comprising repeating steps (a) to (d) for a confirming chromosome other than the chromosome of interest.

3. The method of claim 1, wherein the bin-specific test parameter is reflective of relative abundance of genetic material corresponding to the bin in a maternal test sample.

4. The method of claim 1, wherein obtaining the bin-specific test parameter comprises aligning the sequence reads to a plurality of bins of a reference genome comprising the chromosome of interest.

5. The method of claim 1, wherein obtaining the bin-specific test parameter comprises calculating the bin-specific test parameter based on a total number of sequence reads aligned to each bin.

6. The method of claim 1, wherein the bin-specific test parameter is a normalized bin read count.

7. The method of claim 1, wherein the bin-specific test parameter is produced by the NIPS.

8. The method of claim 1, wherein the method improves a positive predictive value (PPV) of the NIPS to at least 30%, 35%, 40%, 45%, 50%, 55%, 60%, 65%, 70%, 75%, 80%, 85%, 90%, or 95% for human trisomy 21, human trisomy 18 and/or human trisomy 13, as compared to previously available NIPS methods.

9. The method of claim 8, wherein the PPV is improved to at least 93% for human trisomy 21, at least 72% for human trisomy 18, and/or at least 39% for human trisomy 13, as compared to previously available NIPS methods.

10. The method of claim 8, wherein the PPV for trisomy 21 is improved to 98% for human trisomy 21, 92% for human trisomy 18, and/or 69% for human trisomy 13, as compared to previously available NIPS methods.

11. The method of claim 1, wherein the method improves a positive predictive value (PPV) of the NIPS by at least 4%, 10%, 20%, 30%, 40% and 50% for human trisomy 21, human trisomy 18 and/or human trisomy 13, as compared to previously available NIPS methods.

12. The method of claim 11, wherein the PPV is improved by at least 4% for human trisomy 21, at least 20% for human trisomy 18, and/or at least 30% for human trisomy 13, as compared to previously available NIPS methods.

13. The method of claim 1, wherein each bin is about 50 kb long.

14. The method of claim 1, wherein the chromosome of interest is one or more chromosomes.

15. The method of claim 2, wherein the confirming chromosome is one or more chromosomes.

16. The method of claim 1, further comprising:

(a) dividing a confirming chromosome into a plurality of bins, each bin having a chromosomal location;

(b) obtaining a bin-specific test parameter for each bin;

(c) calculating a first sum of bin-specific test parameters for corresponding bins residing on the confirming chromosome; wherein the confirming chromosome is different from a chromosome of interest diagnosed to be aneuploid;

(d) calculating a second sum of bin-specific test parameters for corresponding bins residing on one or more autosomes;

(e) calculating a chromosome representation value for the confirming chromosome by dividing the first sum by the second sum;

(f) comparing the chromosome representation value to a set of references to generate a chromosome-specific comparison result; and (g) detecting the false-positive diagnosis when the chromosome-specific comparison result achieves a predetermined threshold.

17. The method of claim 16, wherein obtaining the bin-specific test parameter comprises sequencing cell-free DNA from a maternal test sample of a pregnant woman carrying the fetus to provide sequence reads.

18. The method of claim 16, wherein obtaining the bin-specific test parameter further comprises aligning the sequence reads to the plurality of bins of a reference genome.

19. The method of claim 16, wherein obtaining the bin-specific test parameter further comprises calculating the bin-specific test parameter based on a total number of sequence reads aligned to each bin.

20. The method of claim 19, wherein the bin-specific test parameter is a normalized bin read count.

21. The method of claim 16, wherein the confirming chromosome is one or more chromosomes in a reference genome.

22. The method of claim 16, wherein the set of references comprises a plurality of chromosome representation values for the confirming chromosome obtained from a random sample of unaffected pregnancies.

23. The method of claim 16, wherein step (f) is performed by calculating a Z-score of said chromosome representation value with respect to the set of references.

24. The method of claim 23, wherein the threshold is achieved when the Z-score is greater than 4.

25. The method of claim 16, wherein the method further comprises assessing a fetal fraction of the cell-free DNA in the maternal test sample before performing step (a).

26. The method of claim 25, further comprising excluding the maternal test sample when the fetal fraction is less than 4%.

27. The method of claim 16, wherein the chromosomal aneuploidy is a complete or partial chromosomal duplication or a chromosomal trisomy.

28. The method of claim 16, wherein the chromosomal aneuploidy is human trisomy 13, human trisomy 18 or human trisomy 21.

29. The method of claim 16, wherein the fetus is aneuploid mosaic.

30. The method of claim 1, wherein GC correction is performed using local polynomial regression (loess).

31. The method of claim 1, wherein performing GC correction includes obtaining the GC content for regions corresponding to the genomic locations of sequenced bins from a reference genome.

* * * * *